United States Patent [19]

Iinuma

[11] Patent Number: 5,425,365
[45] Date of Patent: Jun. 20, 1995

[54] ULTRASONIC DIAGNOSIS APPARATUS UTILIZING DOPPLER TECHNIQUE

[75] Inventor: Kazuhiro Iinuma, Tochigi, Japan

[73] Assignee: Kabushiki Kaisha Toshiba, Kanagawa, Japan

[21] Appl. No.: 36,875

[22] Filed: Mar. 25, 1993

[30] Foreign Application Priority Data

Mar. 26, 1992 [JP] Japan .................................. 4-068004

[51] Int. Cl.6 ............................................... A61B 8/06
[52] U.S. Cl. ........................... 128/660.05; 128/661.09
[58] Field of Search ....................... 128/661.07–661.10, 128/660.04–660.05

[56] References Cited

U.S. PATENT DOCUMENTS

| | | | |
|---|---|---|---|
| 4,257,278 | 3/1981 | Papadofrangakis et al. | 128/661.1 |
| 4,265,126 | 5/1981 | Papadofrongokis et al. | 73/861.25 |
| 4,373,533 | 2/1983 | Iinuma | 128/661.1 X |
| 4,501,277 | 2/1985 | Hongo | 128/661.09 X |
| 4,790,322 | 12/1988 | Iinuma | 128/661.1 |
| 4,913,159 | 4/1990 | Gardin et al. | 128/661.1 |
| 5,010,528 | 4/1991 | Ohtsuki et al. | 367/90 |
| 5,062,427 | 11/1991 | Seo et al. | 128/661.1 |
| 5,090,411 | 2/1992 | Higuchi | 128/660.05 |
| 5,105,813 | 4/1992 | Shikata | 128/660.07 |
| 5,195,521 | 3/1993 | Melton, Jr. et al. | 128/661.1 X |
| 5,280,787 | 1/1994 | Wilson et al. | 128/661.1 |

FOREIGN PATENT DOCUMENTS 0033977 8/1981 European Pat. Off. .
0127157 12/1984 European Pat. Off. .

OTHER PUBLICATIONS

European Search Report dated Jul. 8, 1993.

*Primary Examiner*—Francis Jaworski
*Attorney, Agent, or Firm*—Finnegan, Henderson, Farabow, Garett & Dunner

[57] ABSTRACT

An ultrasonic diagnosis apparatus, in which an ultrasonic image of a diagnostic region of an object having flows of blood is formed, utilizes a Doppler shift for calculating a blood flow amount. For example, first, a plurality of ultrasonic beams are trasnmitted for the diagnostic region and echo signals of the beams are received for forming the ultrasonic image and obtaining Doppler shifts. A measuring line intersecting the flows of blood is delineated on the ultrasonic image. The measuring line orthogonal with the blood flows is preferred. For example, Doppler shift frequancies of the blood flows at measuring points designated on the measuring line are inferred on the basis of the echo signals of Doppler shift already obtaind and memorized. The measuring points are imaginary points in such a case. Using the Doppler shift frequencies of the blood flows, a total amount of blood flows is calculated.

36 Claims, 16 Drawing Sheets

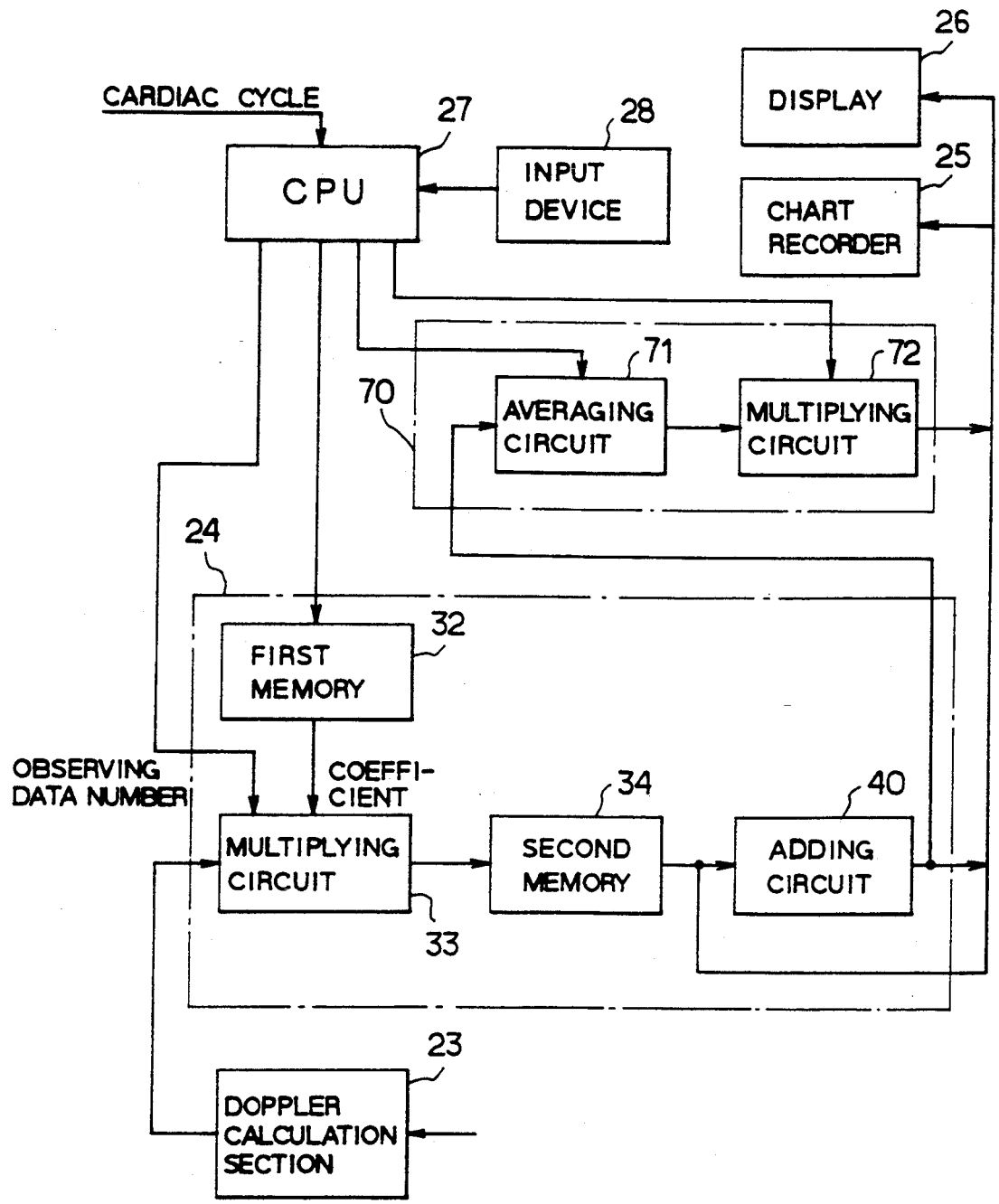
F I G. 10

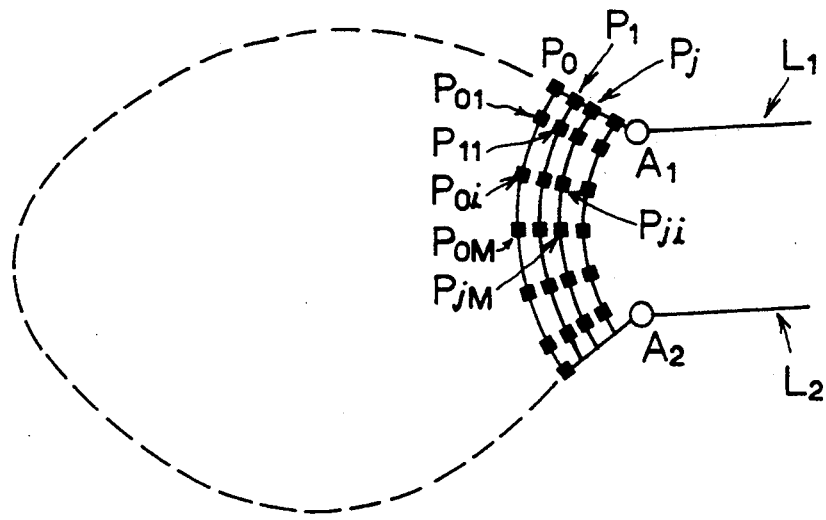
F I G. 11
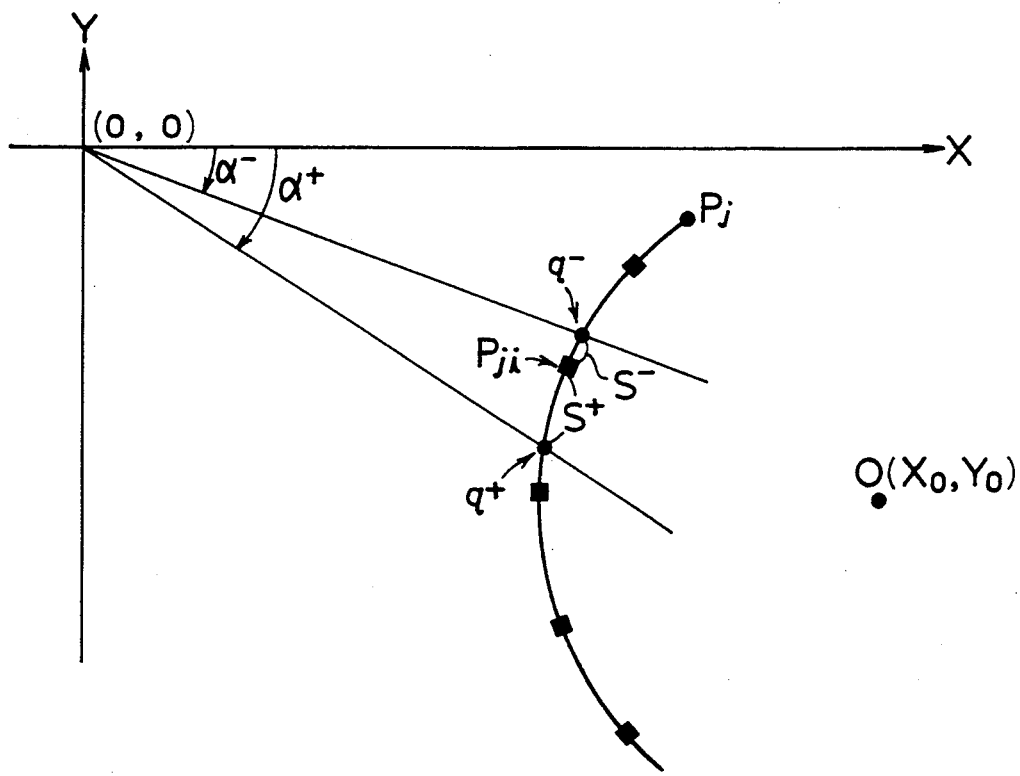
F I G. 12

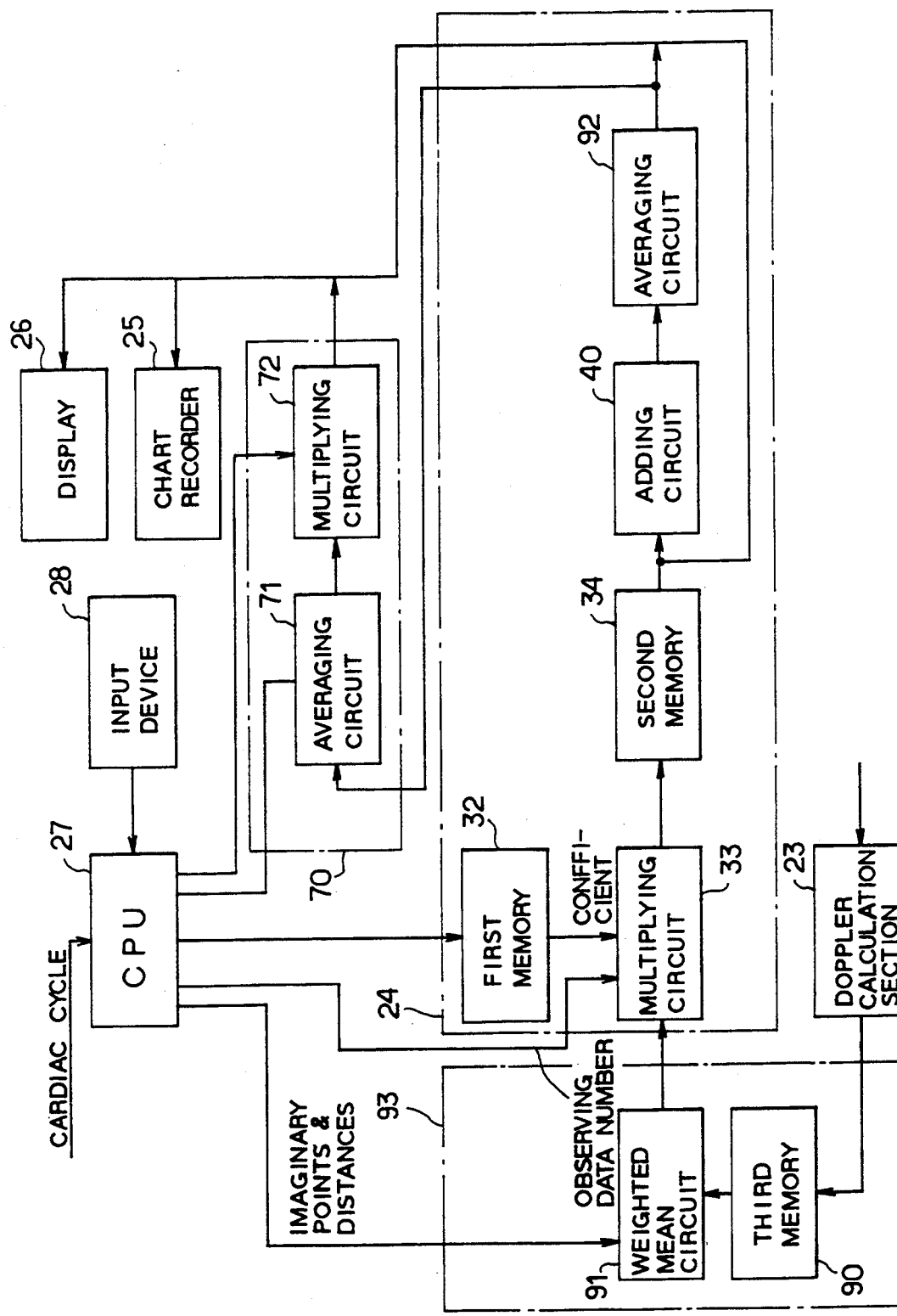
F I G. 14

ULTRASONIC DIAGNOSIS APPARATUS UTILIZING DOPPLER TECHNIQUE

BACKGROUND OF THE INVENTION

The present invention relates to an ultrasonic type blood flow amount measuring apparatus for non-invasively measuring the amount of blood flow through a region of interest of a subject to be diagnosed, through the utilization of an ultrasonic Doppler effect.

In conventional techniques, the ultrasonic Doppler method has been utilized to evaluate the amount of blood flow and the apparatus according to the method is commercially available. The blood flow amount, in such an apparatus, is calculated by employing the ultrasonic Doppler method as follows. Continuous ultrasonic beams from two ultrasonic transducers are emitted to cross at a sampling point of a blood vessel through two different paths. Two ultrasonic Doppler signals derived from receiving echoes are used to determine a blood flow direction and a steering line direction, and thus a velocity of blood flow along the direction of the blood vessel is calculated. A pulsed ultrasonic beam is emitted for calculating the sectional area of the blood vessel determined by the diameter of the blood vessel. Finally, the calculated sectional area and the calculated blood flow velocity are used to calculate the amount of blood flow.

In this case, since the two ultrasonic transducers are required to intersect their ultrasonic beams with each other, a probe containing the two transducers becomes bigger and more complicated in construction. Also an amount of blood flow in the heart of a patient cannot be measured.

A cardiac blood flow or a cardiac output (the amount of the cardiac blood flow per minute), which is delivered from the heart to the whole body, is a particularly important value as body information on diagnosis. However, it is practically difficult to measure the amount of blood flow of an aorta by the conventional method because ultrasonic beams emitted are limited into a certain range and an angle by the existence of the lungs and ribs. Moreover, the cardiac bloodstream, unlike blood vessels, does not have a uniform boundary of a sectional area nor can the direction of the blood flow be determined, therefore, it is even more difficult to measure the amount of blood flow by the conventional method. Extensive research has been conducted, but all the methods are complicated to operate and their precision is poor. Thus, they cannot be put to practical use.

Further, disclosed in U.S. Pat. No. 4,790,322 is an ultrasonic type blood flow amount measuring apparatus. This apparatus includes an ultrasonic transducer for steering a region of interest of a subject with an ultrasonic beam and receiving echoes from the region. There provided is a Doppler calculation section which detects a Doppler shift signal on a line orthogonal with the steering lines. Speeds of blood flows on the line are calculated from the Doppler shift signals, and thus an amount of blood flows passing through the region of interest can be evaluated from the speeds of blood flows and an area of section of the blood flow.

However, this blood flow amount measuring apparatus has a drawback in regard to precision in measurement. Since the measuring line is designated to be orthogonal with the steering lines, it is not guaranteed that the measuring line always properly covers the entire flow of blood. When the line is designated obliquely against the flow, the line sometimes fails to catch a blood flow at its end portions. This results in that a part of the blood flow bypasses the measuring line and leads to reduced precision of measurement.

SUMMARY OF THE INVENTION

Accordingly, it is an object of the present invention to provide an automatic blood flow amount measuring apparatus by which an amount of blood flow from the heart as well as an amount of blood flow in blood vessels can be measured precisely and simply.

It is a further object of the present invention to provide an apparatus by which the heartbeat and the spatial position of blood flows in the heart can be observed.

It is still a further object of the present invention to calculate cardiac output precisely and simply.

It is still a further object of the present invention to be able to designate a measuring line arbitrary by an operator for precise measurement.

It is still a further object of the present invention to provide improved maneuverability for measurement.

These and other objects can be achieved according to the present invention, in one aspect by providing an ultrasonic diagnosis apparatus comprising: an element for forming an ultrasonic image of a diagnostic region of an object having flows of fluid; an element for collecting information of velocity of the fluid at a plurality of measuring points on a measuring line given in the diagnostic region, the measuring line intersecting the flows of fluid; and an element for performing at least either one of display and record of the information of velocity of the fluid.

In another aspect by providing an ultrasonic diagnosis apparatus comprising, in addition to the above forming and collecting elements, an element for calculating an amount of flows of the fluid on the basis of the information of velocity of the fluid.

Preferably, the forming element comprises an element for transmitting a plurality of ultrasonic beams for the diagnostic region and receiving echo signals of the plurality of ultrasonic beams, the plurality of ultrasonic beams consisting of beams for at least tomographic image and Doppler shift signal, an element for memorizing data of the echo signals, and an element for displaying the ultrasonic image based on the data memorized, and the collecting element comprises an element for designating the measuring line on the ultrasonic image, and an element for detecting the information of velocity of the fluid at the measuring points on the measuring line on the basis of the data of Doppler shift memorized by the memorizing element.

Still preferably, the collecting element comprises an element for designating the measuring line on the ultrasonic image, an element for transmitting a plurality of ultrasonic beams for the measuring line and receiving echo signals of the plurality of ultrasonic beams, and an element for detecting the information of velocity of the fluid at the plurality of measuring points on the measuring line, the plurality of ultrasonic beams passing through the measuring points.

It is preferred that the detecting element has a mechanism of calculating Doppler shift frequencies at the measuring points on the basis of the receiving echo signals. It is also preferred that the measuring line is at least approximately orthogonal with the flows of fluid.

The calculating element has a mechanism of multiplying the Doppler shift frequencies by given coefficients.

Still, it is preferable that the diagnostic region is a heart, and the flows of fluid consist of flows of blood of the heart flowing from a left ventricle to an aorta through an aortic valve therein. Preferably, the apparatus further comprises an element for pointing equally spaced points as the measuring points on the measuring line.

Further, it is preferred that the measuring line consists of a plurality of measuring lines, and the lines are at least approximately orthogonal with the flows of fluid. Preferably, the apparatus further comprises an element for postcalculating information of velocity of the fluid at imaginary measuring points on each of the measuring lines by employing weighted mean on the basis of the information of velocity of the fluid detected by the detecting elment. The imaginary measuring points are equally spaced on each of the plurality of arcs. Still, it is preferred to have a mechanism of averaging the amounts of flows of the fluid corresponding to the respective arcs.

Further, it is preferred that the apparatus comprises an element for calculating a cardiac output on the basis of the amount of flows of the blood. Preferably, the cardiac output calculating element has a mechanism of averaging the cardiac output over two or more beats of the heart.

BRIEF DESCRIPTION OF THE DRAWINGS

The accompanying drawings, which are incorporated in and constitute a part of this specification, illustrate embodiments of the present invention and, together with the description, serve to explain the principles of the present invention. In the drawings:

FIG. 10 is a view for showing a circuit diagram of a blood flow amount calculation section according to a second embodiment of the present invention;

FIG. 11 is a view explaining a case of measuring by employing a plurality of arcs;

FIG. 12 is a view explaining a process by employing weighted mean;

FIG. 14 is a view for showing a circuit diagram of a blood flow amount calculation section of the third embodiment;

DESCRIPTION OF THE PREFERRED EMBODIMENTS

Prior to explanation of embodiments of the present invention, a basic principle of the present invention will now be described with reference to FIGS. 1 to 2.

Figure 1:
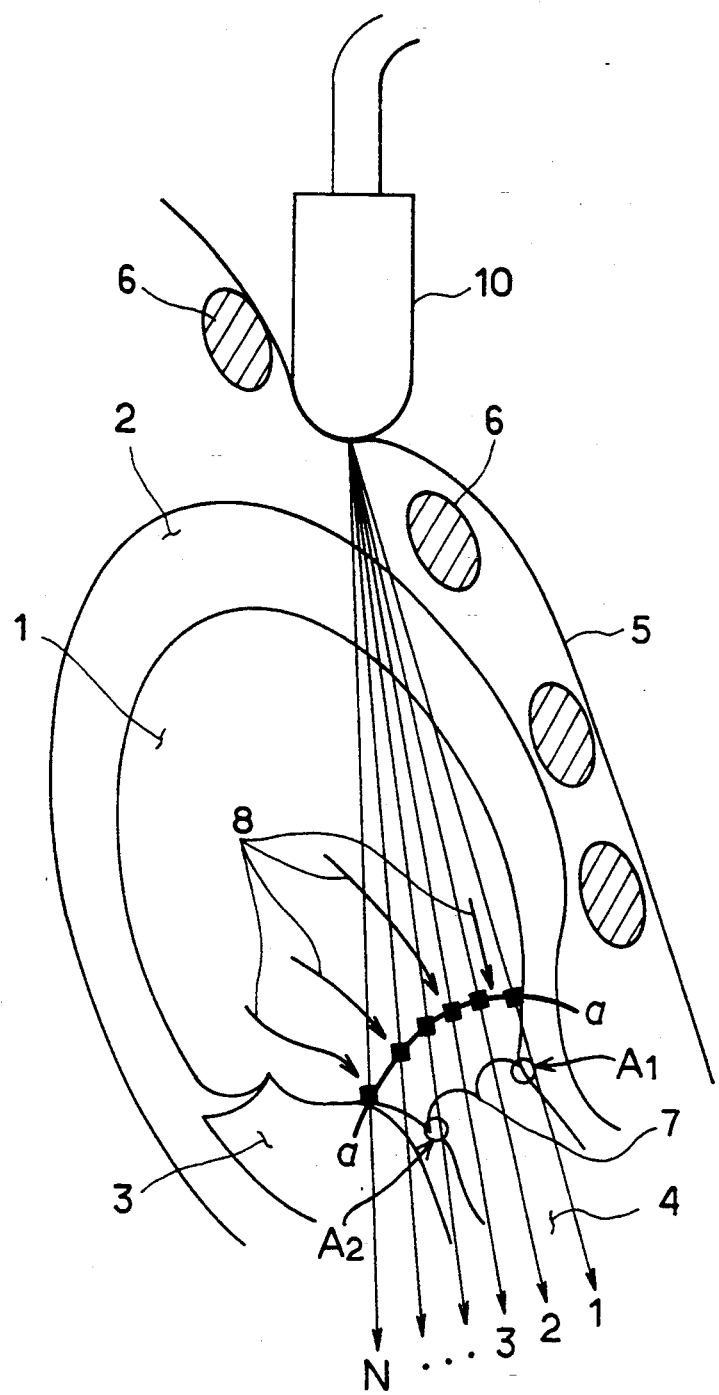
FIG. 1 is a view showing an ultrasonic steering for explaining the principle of the present invention.

In FIG. 1, an ultrasonic probe 10 is placed in intimate contact with a "breast" wall 5 and emits a pulsed ultrasonic beam onto the heart, in a sector steering mode, through a spacing between the ribs 6 and 6 of a human being. Then, an ultrasonic echo pulse reflected in the heart is received by the ultrasonic probe 10. A technique of obtaining a cardiac tomographic image by a B-mode method and a cardiac blood flow image by a color Doppler method (i.e., color flow mapping), with transmitting and receiving ultrasonic beams in changed directions of the steering line, is well known and used for commercially available apparatus, and an explanation of the technique will be omitted here. A description of how the amount of blood flow is measured by detecting a Doppler shift signal will be particularly given.

FIG. 1 shows an observable sectional view of the heart obtained by a B-mode imaging mechanism. A left ventricle 1 functions as a pump that pumps out flows of blood to the whole body and is formed of a cardiac muscle 2. The blood is taken in from a left atrium 3 and sent out from an aorta 4 to the whole body. The blood sent out is prevented from being regurgitated by an aortic valve 7. A boundary portion between the left ventricle 1 and the aortic valve 7 is referred to as an opening of the aortic valve or as an aortic origin (A1, A2).

The foregoing ultrasonic pulse is transmitted and received an n number of times (for example, 8 times) in synchronization with a rate pulse of repetition frequency fr for a steering line 1. Likewise, the transmission and reception of the ultrasonic pulse are repeated within the section that is cut along the center of the left ventricle 1 of the heart and the aorta 4 in the order of steering line 2, 3, ..., N so as to form a sector. A time required for scanning for one time in the section of FIG. 1 (one section) is 25.6 [ms] ($=n\times N/fr=8\times 16/5000$) where $n=8$, $N=16$, and $fr=5$ kHz.

Reception signals corresponding to 8 rate pulses in the steering line 1 direction are, after being phase-detected, converted to digital signals from which Doppler signal components are extracted. A Doppler shift frequency fd is found from the reception information corresponding to the 8 rates and, in this case, it is measured at a time interval (i.e., 800 ns) corresponding to a clock frequency of an A/D converter, for example, 1.25 MHz, along the beam emitted from the ultrasonic probe 10. The time interval of 800 ns becomes around 0.6 mm in terms of the distance. That is, the Doppler shift frequency fd is measured for each of the distances between the sampling points along each steering line. A relation between the Doppler shift frequency fd at a measuring position and the blood flow velocity component $v_B$ at the measuring position in an ultrasonic beam direction is given below:

$$fd = \frac{2 v_B}{C} f_0 \quad (1)$$

where $f_0$ and $C$, respectively, denote the transmission frequency and sound speed (about 1500 m/s) of the ultrasonic beam. In general, the direction of the ultrasonic beam is different from that of the blood flow and, if an angle $\theta$ represents an angle therebetween with the absolute value of the blood flow velocity indicated by $v_0$, then the following equation (2) holds:

$$v_B = v_0 \cos \theta \quad (2)$$

In relation to the directions of the steering lines $2, 3, \ldots, N$, the corresponding Doppler shift frequency fd is found at the respective measuring positions.

Figure 2:
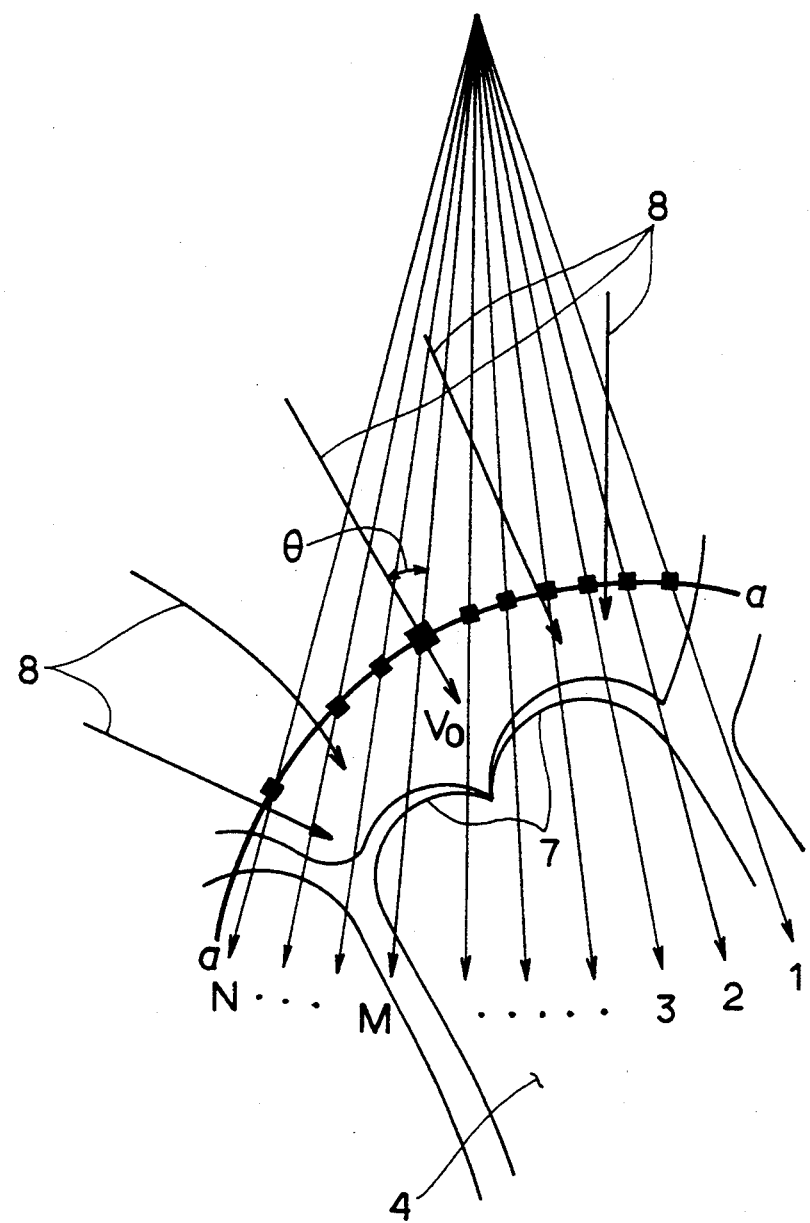
FIG. 2 is an enlarged view of a portion of FIG. 1.

Now, as shown in FIGS. 1 and 2, suppose that there exists a curved line a—a as a measuring line approximately orthogonal with the respective directions $8, \ldots, 8$ of blood flow (the curved line a—a may include a straight line for the blood flow directions $8, \ldots, 8$ being parallel with each other), and that the Doppler shift frequencies at the intersections of respective ultrasonic beams (steering lines) $1, \ldots, N$ and the curved line a—a are represented by $fd_1, fd_2, \ldots, fd_N$.

It will be assumed that the absolute value of a blood flow velocity at the intersection between the curved line a—a and an i-th steering line, that is, the velocity component of the direction that is orthogonal with the curved line a—a, is represented by $V_{0i}$ and the steering line that intersects the center of the curved line a—a is M-th.

Figure 3A:
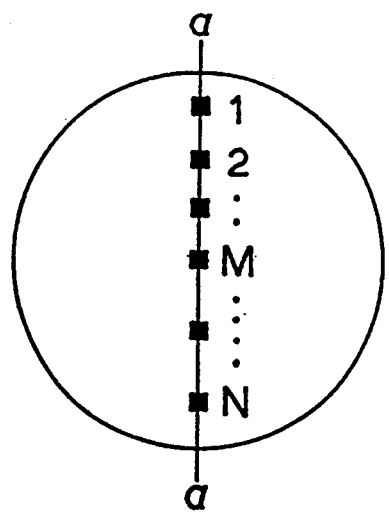
FIGS. 3A to 3C are views for explaining the principle on which the present invention is based.

FIGS. 1 and 2 show a sectional view cut along the major axis of the left ventricle 1 and the center of the aorta 4 and also shows a sectional view of a flow-out route of the left ventricle 1 and the aorta 4 having a circular shape. As shown in FIG. 3A, the intersections are on the center line of the left ventricle flow-out route relative thereto when the circular portion is viewed perpendicularly, that is, from the top left of the drawing. Therefore, the blood flow velocities $V_{0i}$ ($i = 1, 2, \ldots, M, \ldots, N$) at the intersections are found, the whole amount of blood flow Q therethrough can be obtained as follows.

Figure 3B:
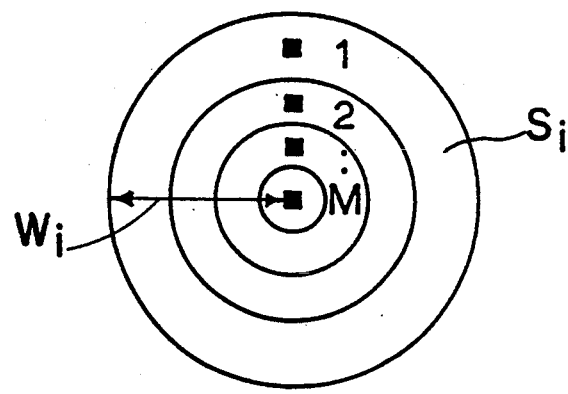
Figure 3C:
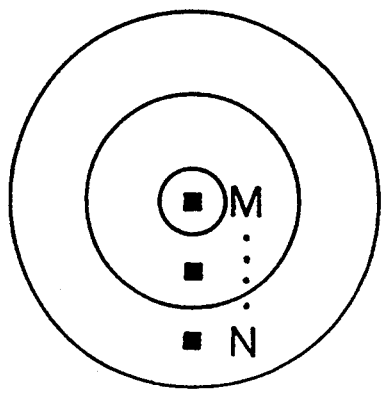

According to the symmetry of the circular, the intersections $1, \ldots, N$, that is, the measuring points shown in FIG. 3A can be divided into two groups; the top half points including the center M (see FIG. 3B) and the bottom half points including the center M (see FIG. 3C).

Let us consider an annulus having the width $W_i$ which passes through each measuring point and the area $S_i$ as shown in FIG. 3B. Supposing that all the velocities at each point in the respective annuluses are equal to each other and are represented by $V_{0i}$ because of the symmetric properties and the amount of blood flow passing through an annulus is $q_i$, the whole blood flow amount $Q_1$ can be shown that:

$$Q_1 = \sum_{i=1}^{M} q_i = \sum_{i=1}^{M} v_{0i} \cdot S_i \quad (3)$$

On the other hand, as illustrated in FIG. 3C, for the bottom half points consisting of $i = M, M+1, \ldots, N$, the whole blood flow amount $Q_2$ can also be given by:

$$Q_2 = \sum_{i=M}^{M} q_i = \sum_{i=M}^{N} v_{0i} \cdot S_i \quad (4)$$

It will now be assumed that $S_M$ represents the area of an annulus having the inside diameter = 0, i.e., the circle. Still, it will be considered that the angles between the directions of the steering lines (that is, the directions of the ultrasonic beams $\alpha_i$) and the blood flow directions (that is, the directions $\beta_i$ being perpendicular to the curved line a—a) are represented by $\theta_i$ at the intersections $P_i$. Then the following equation can be obtained using the equations (1) and (2).

$$v_{0i} = \frac{v_{Bi}}{\cos \theta_i} = \frac{C \cdot fd_i}{2 f_0 \cos \theta_i} \quad (5)$$

When, each $fd_i$, $\theta_i$ then $S_i$ is found, and the blood flow amounts $Q_1$ and $Q_2$ can be obtained from the equations (3) to (5). In general, the smaller the angle $\theta_i$ between the blood flow direction and the ultrasonic beam direction, the better precision of the Doppler detection. Consequently in the example of FIGS. 1 and 2, $Q_1$ may is selected and $Q = Q_1$ is best. However, the average value Q may also be selected as shown in the following equation.

$$Q = \frac{(Q_1 + Q_2)}{2} \quad (6)$$

The basic principle has been described as stated above. But $\theta i$ and $S_i$ are generally rather complicated to be obtained and it is desirable that they practically be measured more simply by rearranging conditions. One example of such an advanced principle will be explained in detail hereinafter with reference to FIGS. 4 and 5.

Figure 4:
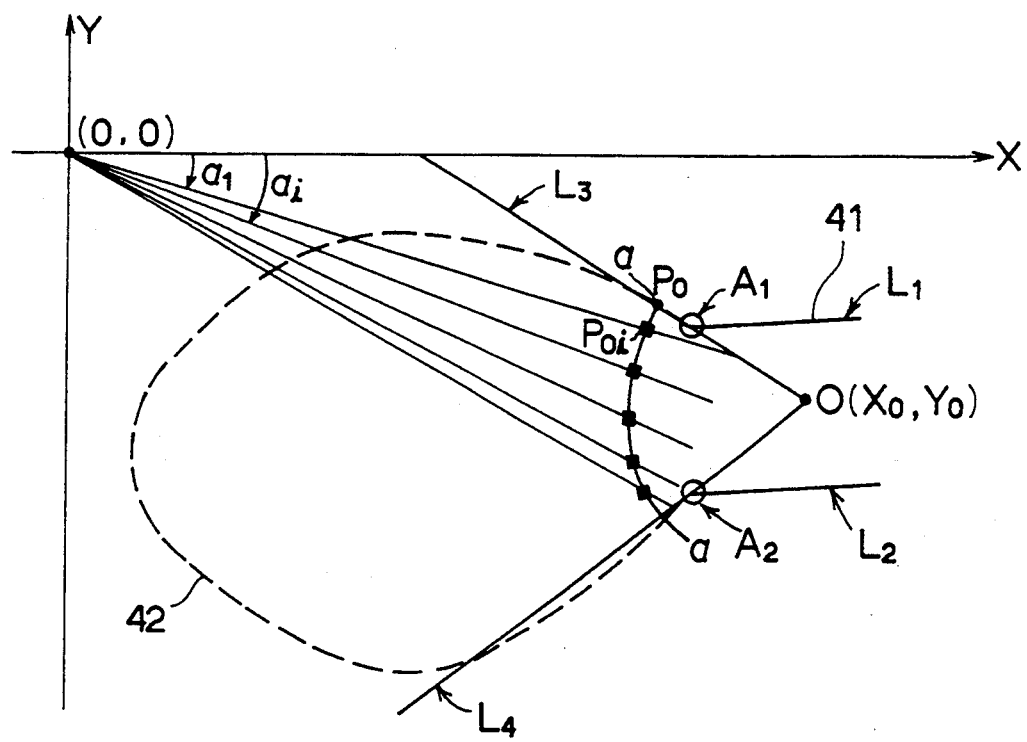
FIG. 4 is a view representing a coodinate according to FIG. 1.
Figure 5:
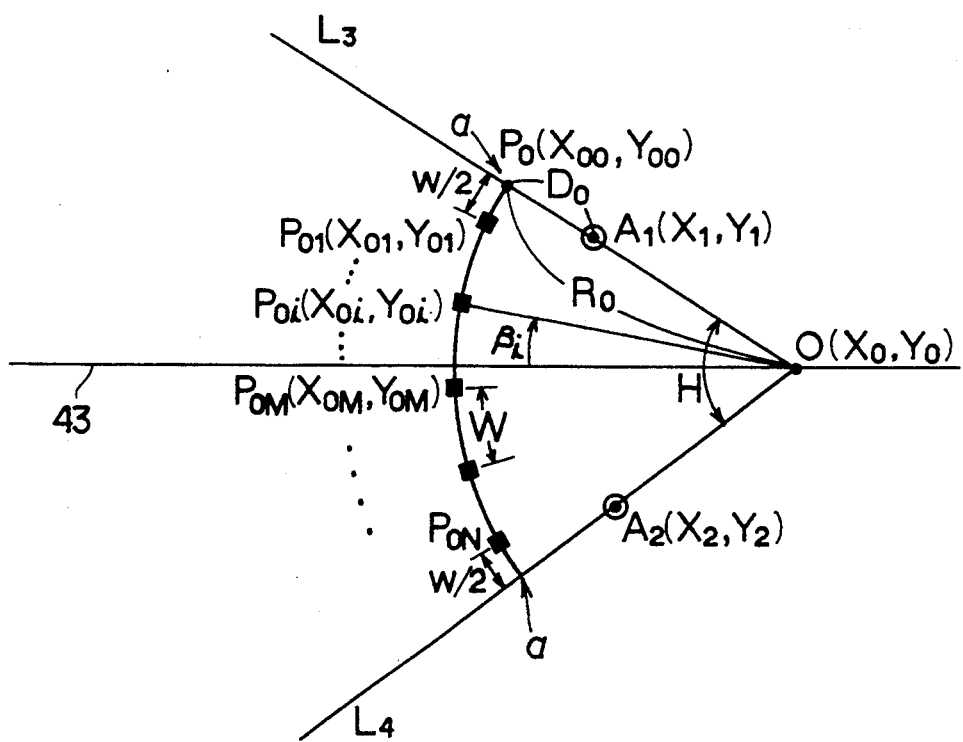
FIG. 5 is an enlarged view of a main part of FIG. 4.

FIG. 4 is a view in which FIGS. 1 and 2 are typically portrayed on coordinate axes and shows a longitudinal sectional view of the inner wall 42 of the cardiac muscle 2 and the inner wall 41 of the aorta 4. FIG. 5 is an enlarged view of the opening of the aortic valve A1 and A2 and neighboring region thereof.

The boundary of the left ventricle 1 and the aorta 4 is the opening of the aortic valve and indicated by $A_1$ ($X_1$, $Y_1$) and $A_2$ ($X_2$, $Y_2$). The intersection point of the straight lines $L_3$ and $L_4$ passing through these points $A_1$ and $A_2$ and contacting the inner wall of the left ventricle 1 is indicated by $O(X_0, Y^0)$. On one of the tangent straight lines $L_3$ and $L_4$ (the line $L_3$, in this case, as shown in the drawing), the point away from the point $A_1$ by the distance $D_0$ is indicated by $P_0$ ($X_{00}$, $Y^{00}$). The first 0 of the subscript here represents information in regard to an arc starting from $P_0$.

The distance between $P_0$ and O is represented by $R_0$. A circular arc having the radius $R_0$ centered at point O is indicated by a curved line a—a substantially perpendicular to the blood flow directions. The intersections $P_{0i}(X_{0i}, Y_{0i})$ between the curved line a—a and the steering lines (ultrasonic beams) $1, \ldots, N$ are measured points of a Doppler shift signal. The angle between the two tangent lines $L_3$ and $L_4$ is indicated by H as shown in FIG. 5, and the measured points $P_{0i}(X_{0i}, Y_{0i})$ are equally spaced (H/N: N = the number of steering lines) on the circular arc a—a where the angles between the measured points $P_{01}$, $P_{0N}$ contacting both the tangent lines $L_3$ and $L_4$ and its tangent lines $L_3$ and $L_4$ are H/2N, respectively. The measured point in the center of the arc a—a is $P_{OM}$.

The coordinates of each point are represented as illustrated in FIGS. 4 and 5. Where the angle between X-axis and each of ultrasonic beams is $\alpha_i$ and the angle between a line 43 parallel to X-axis and the line segment O-$P_{0i}$ is $\beta_i$, the following equations (7) to (15) can be derived. Furthermore, the distance $l_{01}$ from the probe tip (0, 0) to the intersections $P_{0i}(X_{0i}, Y_{0i})$ can be obtained by the equation (14).

$$\theta_i = \alpha_i - \beta_i \tag{7}$$

$$\alpha_i = \tan^{-1}\frac{Y_{0i}}{X_{0i}} \tag{8}$$

$$\begin{bmatrix} X_{0i} = X_0 - R_0 \cos\beta_i \\ Y_{0i} = Y_0 + R_0 \sin\beta_i \end{bmatrix} \tag{9}$$

$$R_0 = \{(X_1 - X_0)^2 + (Y_1 - Y_0)^2\}^{\frac{1}{2}} + D_0 \tag{10}$$

$$\beta_i = \tan^{-1}\frac{Y_1 - Y_0}{X_1 - X_0} - \frac{2i - 1}{2N}H \tag{11}$$

$$H = \tan^{-1}\frac{Y_1 - Y_0}{X_1 - X_0} - \tan^{-1}\frac{Y_2 - Y_0}{X_2 - X_0} \tag{12}$$

$$W_0 = \frac{R_0 \cdot H}{N} \tag{13}$$

$$I_{0i} = (X_{0i}^2 + Y_{0i}^2)^{\frac{1}{2}} \tag{14}$$

$$\begin{bmatrix} S_i(i \neq M) = 2\pi(M - i)W_0^2 \\ S_i(i = M) = \frac{\pi}{4}W_0^2 \end{bmatrix} \tag{15}$$

Using these values, the above-mentioned equations (3) and (4) can be changed into as follows:

$$Q_1 = \sum_{i=1}^{M} v_{0i} \cdot S_i \tag{16}$$

$$= \frac{\pi C W_0^2}{f_0}\left\{\sum_{i=1}^{m-1}\frac{(M-1) \cdot f d_i}{\cos\theta_i} + \frac{f d_M}{8\cos\theta_M}\right\}$$

$$Q_2 = \sum_{i=M}^{N} v_{0i} \cdot S_i \tag{17}$$

$$= \frac{\pi C W_0^2}{f_0}\left\{\sum_{i=M+1}^{N}\frac{(M-i) \cdot f d_i}{\cos\theta_i} + \frac{f d_M}{8\cos\theta_M}\right\}$$

$W_0$ and $\theta_i$ in the equations (16) and (17) can be obtained by the equations (7) and (13) if $D_0$ (the distance between $P_0$ and $A_1$), O($X_0$, $Y_0$), $A_1$($X_1$, $Y_1$), and $A_2$($X_2$, $Y_2$) are given.

The angles of the steering lines 1, ..., N of ultrasonic beams are determined on the basis of the angle $\alpha_{01}$ of the most exterior steering line 1 and are represented as "$\alpha_{0i}-\alpha_{01}$" by the equation (8). Such angles can be achieved by setting up the delay time corresponding to "$\alpha_{0i}-\alpha_{01}$" by using a scanning control circuit of ultrasonic diagnostic equipment.

The equations (3) and (4), or (16) and (17) are simply calculated by adding and multiplying, and thus can be calculated at high speed via hardware. However, they are preferably calculated as follows in terms of the process speed.

An explanation will be given hereinafter by employing the equation (16). The values $W_0$, $\pi$, C, $f_0$ and M in the equation (16) are known values regardless of the amount of the blood flow in the region where the measurement is carried out, and the value of $\theta_i$ remains constant by designating a curved line a—a and its intersections while the amount of blood flow is measured. Hence, these values are not necessarily calculated at high speed in real time. Instead, they are calculated by the equations (7) and (13) in the CPU 27 in advance, and coefficients $B_i$ can be summerized and calculated by the following equation (18).

$$\begin{bmatrix} B_i(i \neq M) = \frac{\pi C W_0^2}{f_0} \cdot \frac{(M-i)}{\cos\theta_i} \\ B_i(i = M) = \frac{\pi C W_0}{8 f_0} \cdot \frac{1}{\cos\theta_M} \end{bmatrix} \tag{18}$$

Therefore, the foregoing equation (16) may be simplified as follows:

$$Q_1 = \sum_{i=1}^{M} B_i \cdot f d_i \tag{19}$$

By the same manner, the foregoing equation (17) may be simplified as follows:

$$Q_2 = \sum_{i=1}^{N} B_i \cdot f d_i \tag{20}$$

A first embodiment of the present invention will now be explained below on the aforementioned principle.

Figure 6:
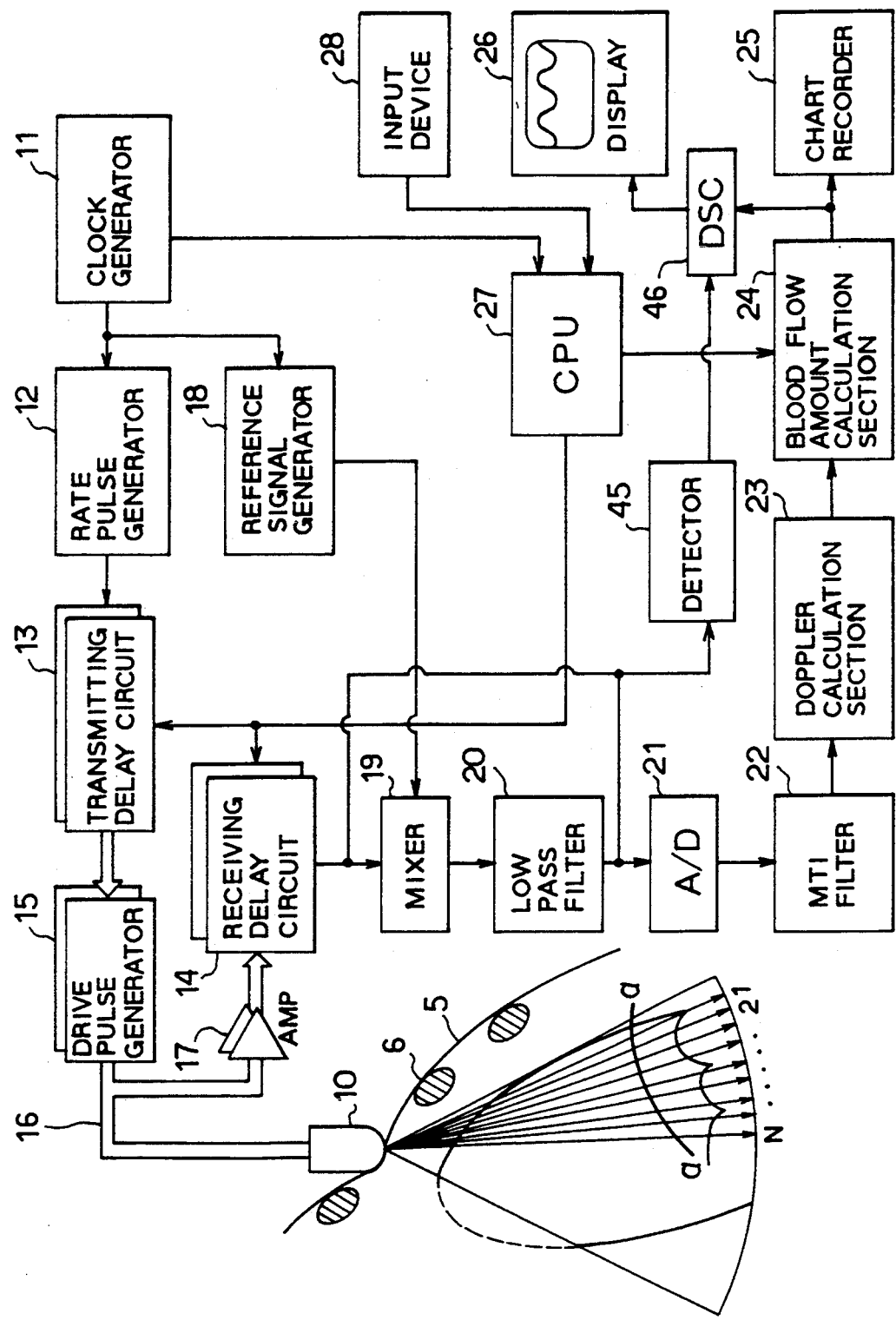
FIG. 6 is a view showing an ultrasonic diagnosis apparatus according to a first embodiment of the present invention.

In the embodiment shown in FIG. 6, there is provided a clock generator 11. The clock generator 11 delivers a fundamental clock of, for example, 40 MHz to a rate pulse generator 12. The rate pulse generator 12 in turn delivers a rate pulse of 5 kHz, on the basis of the fundamental clock, to a transmitting delay circuit 13. The transmitting delay circuit 13 serves to delay the rate pulse in accordance with the steering directions and is connected to drive a pulse generator 15. The drive pulse generator 15 is comprised of a plurality of pulsers which are connected to an ultrasonic probe 10 through cables 16.

The ultrasonic probe 10 has a plurality of ultrasonic transducers. The transducers are driven by the drive pulses from the pulsers and transmit ultrasonic beams to a region of interest of an object and receive echoes from the object. The echo signals from the ultrasonic probe 10 are connected through an amplifier 17 to a receiving delay circuit 14. The delay circuit 14 is set to a delay time corresponding to the delay time of the delay circuit 14 and extracts a reception signal corresponding to each of the respective steering lines.

The output of the delay circuit 14 is connected to a mixer 19 which in turn carries out phase detection of a reception signal through the multiplication of reference signals (for example, 2.5 MHz) from a reference signal generator 18 and the reception signal from the delay circuit 14. The mixer 19 is comprised of a 2-channel mixer circuit so as to find the normal and reverse directions of a Doppler signal from the reception signal. The same reception signal is supplied to both of the channels of the 2-channel mixer circuit, noting that reference signals whose phases are exactly 90 degree shifted with each other are supplied to the reference input terminals of the two-channel mixer circuit for the multiplication therein.

The output terminal of the mixer 19 is connected to an MTI (Moving Target Indication) filter 22 through a low-pass filter 20 and an A/D converter 21. The low-pass filter 20 is provided to remove an unwanted high-pass component from the signal of the mixer 19. The MTI filter 22 is provided to eliminate an echoed wave component which comes from a slow motion region such as the cardiac muscle. The output terminal of the MTI filter 22 is connected to a Doppler calculation section 23 for calculating a Doppler shift frequency fd.

The output terminal of the Doppler calculation section 23 is connected to a blood flow amount calculation section 24. Based on the Doppler frequency signal from the Doppler calculation section 23, the blood flow amount calculation section 24 evaluates, with use of equations (3), (4) and (6), (16), (17) and (6), or (19), (20) and (6), the amount of blood flow by the values fd, ... , fd at the intersection between each steering line 1 (2, .., N) and a single curved line a—a perpendicular to the directions of the blood flows.

The blood flow amount calculation section 24 is connected at its output to a chart recorder 25 and through a digital scan converter(DSC) 46 to a display 26. It is to be noted that a CPU(central processing unit) 27 controls the blood flow amount calculation section 24 and the transmitting and receiving delay circuits 13 and 14. An input device 28, such as a trackball and/or a mouse, is coupled to the CPU 27 for measurement operation. The input of an imaging section 45 for B-mode images and colour blood flow images are connected to the delay circuit 14 and the low-pass filter 20, its output being supplied through the DSC 46 to the display 26.

Figure 7:
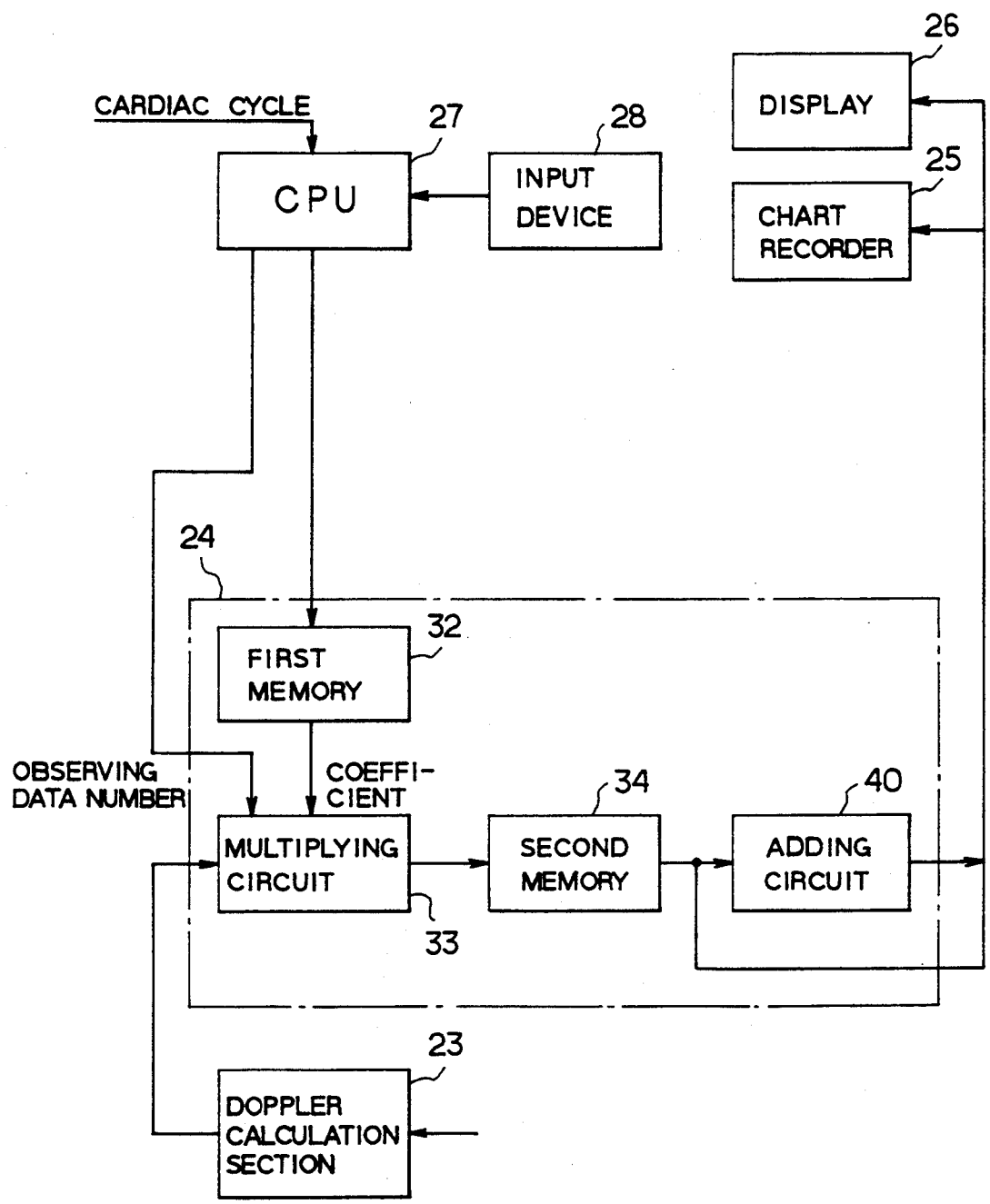
FIG. 7 is a view for showing a circuit diagram of a blood flow amount calculation section shown in FIG. 6.

As shown in FIG. 7, the blood flow amount calculation section 24 includes a first memory 32 for storing the coefficients $B_i$ which are precalculated by the CPU 27. The output of the first memory 32 is connected to a multiplying circuit 33 which multiplies the output coefficients $B_i$ from the first memory 32 by the Doppler shift frequencies fd, ... , fd from the Doppler calculation section 23.

The output of the multiplying circuit 33 is connected through a second memory 34 to an adding circuit 40. The second memory 34 stores the output of the multiplying circuit 33 for a period. The adding circuit 40 adds the outputs from the second memory 34. The output from the adding circuit 40 is supplied to the chart recorder 25 and to the display 26.

An example of the operational process, which is carried out by the CPU 27 according to FIG. 8, will be given hereinafter with reference to FIGS. 4 and 5.

Figure 8:
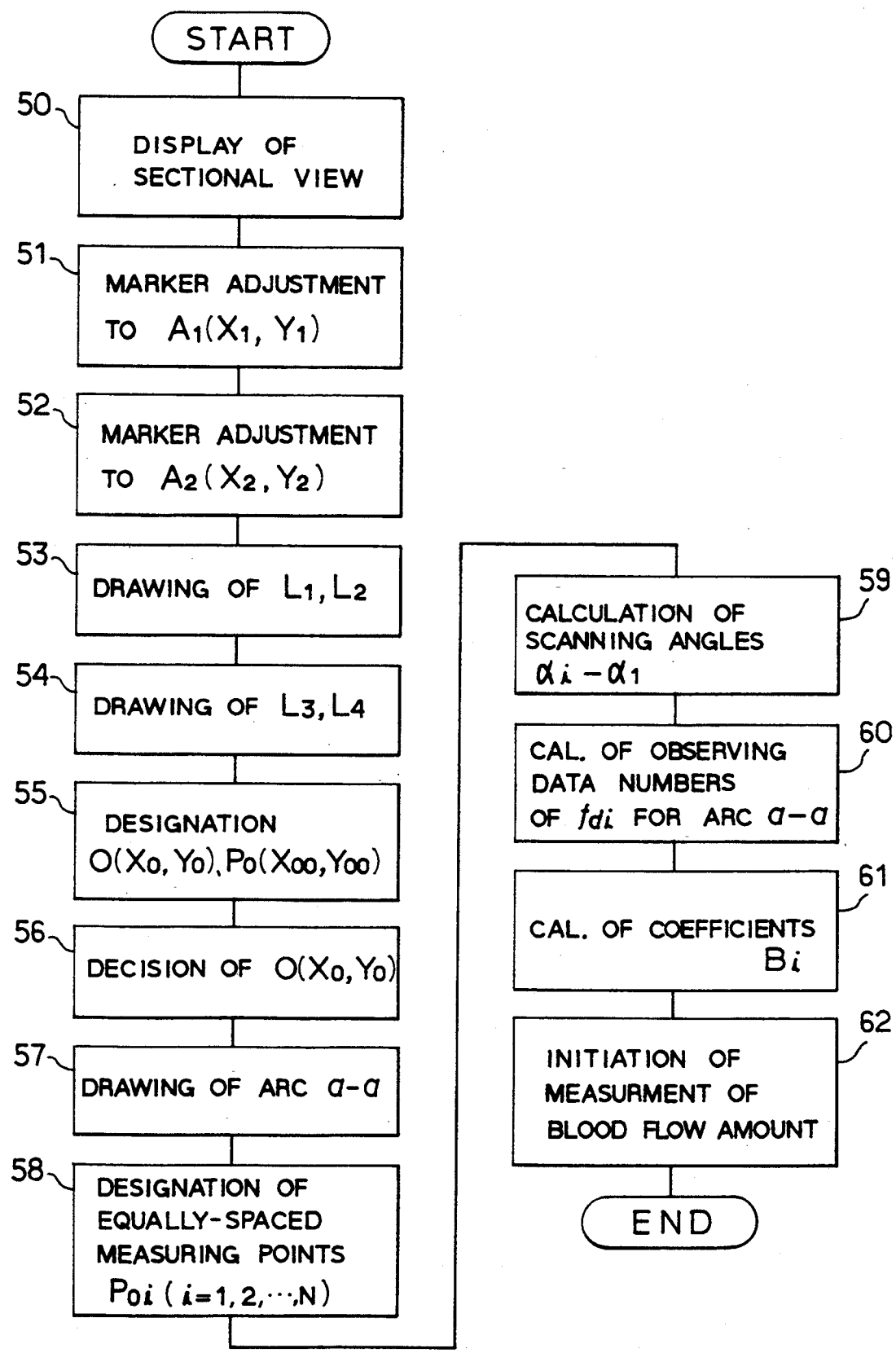
FIG. 8 is a flow chart carried out by a CPU.

First, at Step 50 in FIG. 8, under control of the CPU 27, a sectional view of the major axis of a patient's heart is delineated on the display 26 by employing an ultrasonic tomography image (including the color Doppler image superimposed thereon), as shown in FIG. 1. Then at Step 51, a marker is adjusted and fixed on the aortic origin $A_1$ ($X_1$, $Y_1$) by using the input device 28, as shown in FIG. 4. Thus, the coordinate ($X_1$, $Y_1$) of $A_1$ is determined.

Next at Step 52, another marker is adjusted and fixed on the aortic origin $A_2$ ($X_2$, $Y_2$) facing opposite to $A_1$ ($X_1$, $Y_1$), and the coordinate ($X_2$, $Y_2$) of $A_2$ is determined.

Subsequently, at Step 53, line segments $L_1$ and $L_2$ are drawn. That is, a line passing through the two markers is determined and then line segments $L_1$ and $L_2$ are determined in the direction for the aorta 4 (i.e., the direction perpendicular to the marker-passing line from the origin $A_1$ and $A_2$, respectively) on the display 26.

Then at Step 54, another pair of line segments $L_3$ and $L_4$ whose angles are predetermined with respect to $L_1$ and $L_2$ are also drawn from the aortic origins $A_1$ and $A_2$ in the direction for the left ventricle 1 on the display 26.

Then at Step 55, the intersection point $O(X_0, Y_0)$ between $L_3$ and $L_4$ is made, and the point away from $A_1$ by a determined distance $D_0$ on the line segment $L_3$ is represented as $P_0$ ($X_{00}$, $Y_{00}$). At step 56, the position of the intersection point $O(X_0, Y_0)$, that is, the coordinate ($X_0$, $Y_0$) is moved by using the input device 28 so that the line segment $L_3$ and $L_4$ are fixed to contact the inner wall of the left ventricle 1, respectively. Thus, the coordinate ($X_0$, $Y_0$) is determined.

After the above-mentioned preparation, at Step 57, the CPU 27 delineates an arc (which corresponds to a curved line a—a shown in FIG. 1), centered at the point $O(X_0, Y_0)$, starting from $P_0$ ($X_{00}$, $Y_{00}$) to a intersection which intersect the other line segment $L_4$. Then at Step 58, the equally spaced measuring points $P_{0i}$ at the number of N (i=1,2, ... , M, ... , M) are placed on the arc a—a.

Provided that the angle between $L_3$ and $L_4$ is H, the spacing between these points is represented as "$H.R_0/N$" ("H/N" from the angle point of view), $R_0$ is the distance between the point $O(X_0, Y_0)$ and the point $P_0$ ($X_{00}$, $Y_{00}$), as expressed in the equation (10). The distance between the point $P_0$ and the point $P_{01}$ is "$H.R_0/2N$" (that is, ½ of the distance of the adjacent spacing) and the distance of the final spacing of the arc is also determined as "$H.R_0/2N$". Thus, the coordinates ($X_{0i}$, $Y_{0i}$) of $P_{0i}$ are determined.

Then, at Step 59, the scanning angles "$\alpha_i - \alpha_1$" of the ultrasonic beam is calculated according to the equation (8).

Figure 9:
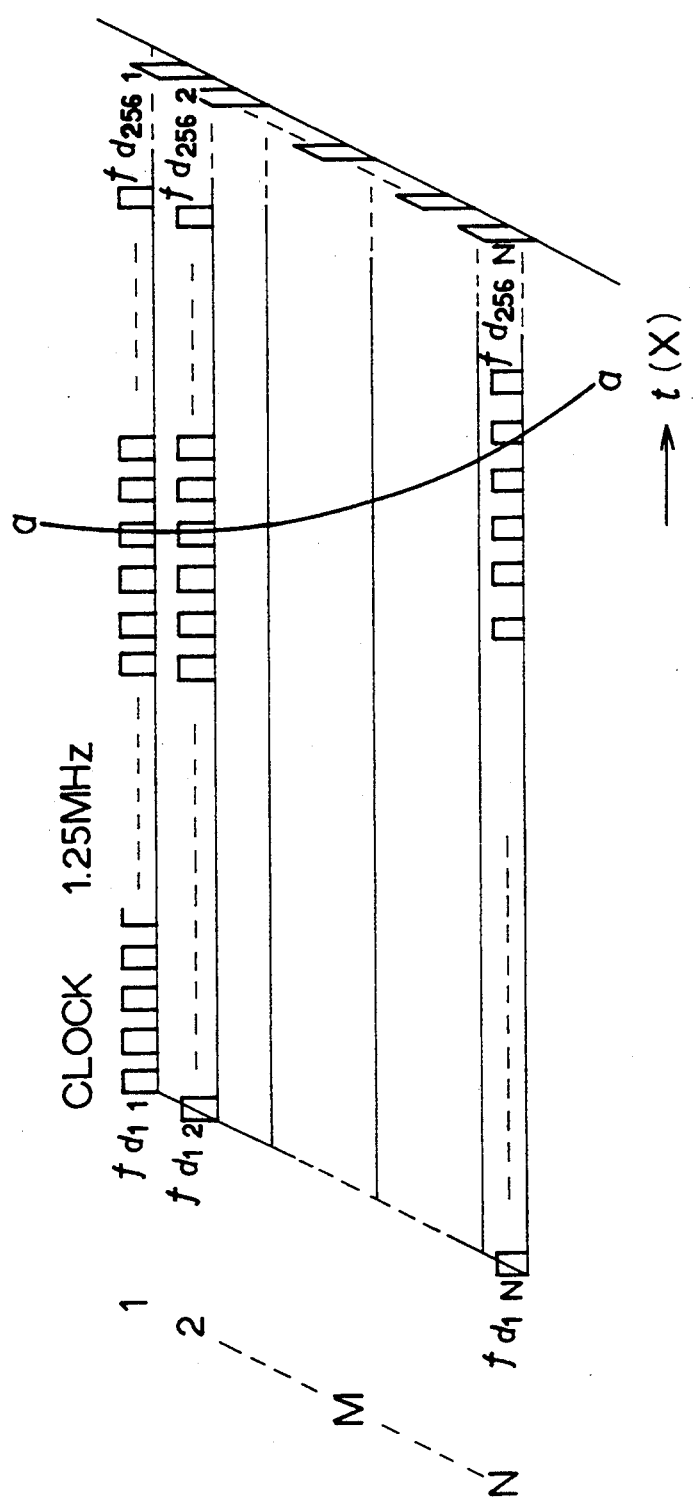
FIG. 9 is a time chart showing relation between drive pulses and a single arc.

After the above procedure having being completed, at Step 60, the CPU 27 determines the observing data numbers of $fd_i$ designating the arc a—a on the output sequence from the Doppler calculation section 23 (refer to FIG. 9).

The observing data numbers are as follows. For example, the value $fd_1$ for the direction of the first steering line 1 in FIG. 1 is output from the Doppler calculation section 23 at 1.25 MHz, in other words, per 0.8 μsec (equivalent to 0.6 mm in the form of the distance). Thus, if 256 pieces of data are utilized, the data is collected during 205 μsec (=0.8 μsec×256), which is equivalent to 15.4 cm in the form of the distance. These collected values are represented as $fd_{11}$, $fd_{21}$, ... , $fd_{25\ 61}$ for convenience, as shown in FIG. 9. Likewise, the data $fd_{12}$, $fd_{22}$, ... , $fd_{256\ 2}$ can be collected for steering line 2.

Carrying out the above data collection for all the directions of the steering lines 1 to N produces an imaginary data map shown in FIG. 9. In FIG. 9, reference numerals 1, 2, ..., M, ..., N represent the steering lines in FIG. 1 and the horizontal axis represents the time t(X) for each of the steering lines, whose each start time is matched.

Then, the arc a—a designated at Step 57 is assigned on the imaginary data map of FIG. 9, and the observing data numbers according to the arc a—a (i.e., corresponding to the measuring points $P_{0i}(i=1, \ldots, N))$ can be determined line by line in the data map.

Each of the observing data numbers (i.e., the measuring points $P_{0i}$) has a different distance from the ultrasonic probe 10. But, since the observing data number increases by 0.6 mm per period of 1.25 MHz, the number that exactly intersects the arc a—a can be determined by calculation among the 256 points for each $fd_i$.

Further, at Step 61, the CPU 27 calculates the coefficients $B_i$ according to the foregoing equation (18).

Then the CPU 27 will go into next Step 62, where the measurement is initiated by sending signals to various circuits therein, the signals including the delay time signals to transmitting and receiving delay circuits 13 and 14 and the coefficient signal and the observing data number signal to the first memory 32 and the multiplying circuit 33 of the blood flow amount calculation section 24.

The aforementioned preparation allows the steering line of the ultrasonic beam to pass through the respective measuring points $P_{0i}$ during the measurement.

The operation of the aforementioned ultrasonic diagnosis apparatus will now be explained below.

A clock is delivered from the clock generator 11 to the rate pulse generator 12, which in turn generates a rate pulse of 5 kHz on the basis of the clock. The rate pulse generator 12 supplies the rate pulse to the transmitting delay circuit 13 where it is delayed at the delay time instructed to the sector steering direction 1 (, . . . , N). The delayed rate pulse is supplied to the drive pulse generator 15, which delivers a drive pulse corresponding to that delay time. The drive pulse is supplied to the ultrasonic transducers of the ultrasnonic probe 10, which emits corresponding ultrasonic beams in the direction of the steering line 1 (, . . . , N). The ultrasonic beam travels into the heart and at this time the echoes from that living tissues sequentially return to the probe 10 in accordance with the depth of the living tissues. The echoes received are converted into electric echo signals therein.

The echo signals are, after being amplified by the amplifier 17, supplied to the receiving delay circuit 14 where they are sequentially delayed by the delay time equal to that of the transmitting delay circuit 13. At this time the echo signals are added together. The output signal of the receiving delay circuit 14 is input to the mixer 19 where it is phase-detected. The output signal of the receiving delay circuit 14 is also amplitude detected by the imaging section 45, and then enters into the display 26 where it is displayed as a real time B-mode image.

The echo signal is, after being phase detected by the mixer 19, supplied through the low-pass filter 20 to the A/D converter 21 and to the imaging section 45 for color flow mapping. The A/D converter 21 converts the echo signal to a digital one in response to a clock signal with a frequency of 1.25 MHz. The echo signal, thus converted, is supplied through the MTI filter 22 to the Doppler calculation section 23.

An ultrasonic pulse transmitted in response to one period of the rate pulse from the ultrasonic probe 10 travels within the subject in a certain direction, and correspondingly, echo signals (pulses) are returned one after another from body tissues to the probe 10. The deeper the ultrasonic pulse goes into the body from its surface, the longer the time required for the echo signals to return is in proportion to the distance from the body surface. In this embodiment, the A/D conversion of the echo signals are executed at a time interval of 1.25 MHz. The sampling of the echo signal at 1.25 MHz is analogous to sampling the echo signal for every 0.6 mm of distance in the depth direction from the surface with the sound speed calculated as 1500 m/s. The ultrasonic beam direction is controlled as described above with reference to FIG. 1, and thereby a total of 8 pieces of data can be obtained per each spacing of 0.6 mm from the body surface.

The Doppler calculation section 23 calculates the Doppler shift frequencies fd, . . . , fd by the input echo signals. The Doppler shift frequency fd is calculated for each measuring point at the spacing of 0.6 mm along each steering line from 1 to N. The calculation result is input into the blood flow amount calculation section 24 and provided for the calculation of the amount of blood flow.

In the blood flow amount calculation section 24, the Doppler shift frequencies $fd_{11}$, $fd_{21}$, . . . , $fd_{256\ 1}$, $fd_{12}$, $fd_{22}$, . . . , $fd_{256\ 2}$, . . . for 8 rate pulses are supplied in turn to the multiplying circuit 33. Stored in the first memory 32 is the coefficient $B_i$, which had been precalculated, the coefficient $B_i$ being supplied to the multiplying circuit 33. This circuit 33 also receives the observing data numbers from the CPU 27. Thus, when the Doppler shift frequencies $fd_i$ in accordance with the designated observing data numbers come in, the circuit 33 carries out the multiplication "$B_i.fd_i$". The multiplication result "$B_i.fd_i$" for each steering line is then sent to the second memory 34, thus being temporarily stored therein.

After completing the scan of the N steering lines, the stored data "$B_i.fd_i$" for the N steering lines are sent not only to the adding circuit 40 but also to the display 26 and the chart recorder 25. Thus, the data "$B_i.fd_i$" for the N steering lines are added according to the equations (19) and (20) and further averaged according to the equation (6) therein. The addition result, that is, the amount of blood flow desired to be measured, is then sent to both the display 26 and the chart recorder 25 for showing the amount of blood flow in a mode of the amount versus elapsed time.

In the blood flow amount calculation section 24, instead of the coefficients $B_i$ used above, the amount of blood flow may be repeatedly calculated according to the foregoing equations (3), (4) and (6), or (16), (17) and (6). The time required for N rates (one section) is 25.6 ms here as described before, thus the whole amount of blood flow Q can be obained for the arc a—a and be displayed every period of 25.6 ms.

In this embodiment, utilizing the output of the second memory 34, the blood flow velocities at any measuring point can be displayed on the display 26 and/or the chart recorder 25 in a mode of the amount versus elapsed time.

As will be understood from the foregoing description, the apparatus in this embodiment transmits and receives ultrasonic beams toward an object, thereby detecting the Doppler shift frequencies from echo signals. Using the detected Doppler shift frequencies, calculation for an amount of blood flow is made on the intersections on a designated curved line at which blood flows intersect to the curved line. Hence, the amount of blood flow in organs whose blood flow direction is not clearly determined, such as in a heart, as well as the blood flow in blood vessels, can be automatically measured and displayed in real time, and the beating of the heart and the condition of blood vessels spatially running can be observed at the same time.

In particular, the foregoing blood flow amount calculation section 24 adopts, in the multiplication, coefficients representing a physical value of the sectional area of a blood flow to be measured. The coefficients make the multiplication remarkably simple and culculation load reduced.

Moreover, the curved line is designated to be apporoximately orthogonal with blood flows themselves. Thus it is possible to designate measuring points in a section orthogonal with the blood flows and to adequately detect Doppler shifts in the section desired to be measured. This technique surely eliminates a situation in which the measuring points are placed in a section substantially leaning in a parallel way to blood flows. In such a leaning case of the section, it was worried that a velocity of blood flow might be changed with its passing direction, thereby detected values sometimes being different from true values originally wanted. But the apparatus of this embodiment is able to prevent such leaning of the detecting cross-section, thus providing greater precision in measurement compared to the conventional apparatus in which a curved line is designated to be orthognal with steering lines.

The apparatus of this embodiment also functions as an ordinary ultrasonic diagnosis apparatus. Since it is able to display a real time B-mode image of an object by performing amplitude detection of the output from the receiveing delay circuit 14 and to measure the amount of blood flow of a desired region, it is believed that it can provide extremely useful information for medical diagnosis. Furthermore, since it employs ultrasonic waves, it is non-invasive towards an object, and since it is extremely simple, it can measure the amount of blood flow as many times as necessary, even if the object is seriously ill.

A second embodiment of the present invention will now be explained according to FIG. 10.

The present embodiment relates to calculation of cardiac output. It is necessary to obtain the average of the outputs at least for one heartbeat in order to obtain the cardiac output. Moreover, averaging cardiac outputs for a plurality of times of heartbeats can produce increased measurement precision. Therefore, the present embodiment adopts, for example, 10 heartbeats for the averaging.

As shown in FIG. 10, there provided is a cardiac output calculation section 70 in the apparatus. The cardiac output calculation section 70 includes an averaging circuit 71 and a multiplying circuit 72, which are connected in turn to the output of the adding circuit 40. The CPU 27 is designed to receive a signal of cardiac cycle.

The averaging circuit 71, under control of the CPU 27, receives the amount data of blood flow for ten times of heartbeats and averages them therein. The averaged data is then supplied to the multiplying circuit 72 to which a signal of heart rate (per minute) is provided from the CPU 27. Thus, the cardiac output is calculated by multiplying those values therein and supplied to the display 26 and the chart recorder 25.

As a result, the cardiac output of higher measurement precision can be obtained as well as the same advantages as in the first embodiment.

A third embodiment of the present invention will now be described with reference to FIGS. 11 to 15. The present embodiment can further increase precision in measurement of the amount of blood flow.

In the above-mentioned examples, the measurement of $fd_i$ has been carried out using one arc a—a (one curved line) starting from the point $P_0$. Nevertheless, the value $fd_i$ can be measured at the same time at each measuring point on each steering line, as will be described hereinafter. Consequently, as shown in FIG. 11, a plurality of arcs $P_0, P_1, \ldots, P_j, \ldots$ may be formed and the values obtained by measurement on each arc are added and averaged, thereby further increasing precision. If the coordinates of $P_j$ is $(X_j, Y_j)$ and the coordinates of the intersection $P_{ji}$ on the arcs are $(X_{ji}, Y_{ji})$, it can be shown that:

$$\begin{bmatrix} X_{ji} = X_0 - R_j \cos\theta_i \\ Y_{ji} = Y_0 + R_j \sin\beta_i \end{bmatrix} \quad (21)$$

$$R_j = \{(X_1 - X_0)^2 + (Y_1 - Y_0)^2\}^{\frac{1}{2}} + D_j \quad (22)$$

wherein $D_j$ is the distance between the points $A_1$ and $P_j$.

When a plurality of arcs are employed, the intersections between the arcs and the steering lines are not necessarily equally spaced on each of the arcs. In this case, therefore, the virtual equally spaced points, which are different from the actual intersections (measured points), may be placed on the arcs, and the values of the imaginary points may be inferred by weighted mean of the values of the measured points on the respective arcs and may be employed.

As described above, the other arcs, except for $P_{0i}$, can be handled in the same way by replacing $P_{ji}(X_{ji}, Y_{ji})$ with the imaginary points (all of them are equally spaced). Such a concept can eliminate the need for the special control of the ultrasonic beam directions as stated above by which the intersections between the steering lines and the arcs are equally spaced.

With reference to FIG. 12, it will be hereinafter given a method of inferring the value $fd_i$ on $P_{ji}$ from the measured values $fd_i^-$, $fd_i^+$ at intersections (measured points) $q^-$ $(\xi^-, \eta^-)$, $q^+$ $(\xi^+, \eta^+)$ on both sides of an imaginary point $P_{ji}(X_{ji}, Y_{ji})$ on the j-th arc starting from $P_j$.

Where measured points on both adjacent sides to the imaginary point $P_{ji}$ are selected and the distances between the point $P_{ji}$ and the both measured points are $S^-$, $S^+$, respectively, $fd_i$ can be given by:

$$fd_i = \frac{(S^- fd_i^+ + S^+ fd_i^-)}{(S^- + S^+)} \quad (23)$$

Therefore, the following equation can be further obtained:

$$\begin{bmatrix} S^+ = \{(\xi^+ - X_{ji})^2 + (\eta^+ - Y_{ji})^2\}^{\frac{1}{2}} \\ S^- = \{(\xi^- - X_{ji})^2 + (\eta^- - Y_{ji})^2\}^{\frac{1}{2}} \end{bmatrix} \quad (24)$$

where the values of $\xi^-$, $\eta^-$, $\epsilon^+$, $\theta^+$ can be found by the following simultaneous equations employing the angles $\alpha^-$, $\alpha^+$ of the steering lines shown in FIG. 12:

$$\begin{bmatrix} \eta = -\xi \tan\alpha \\ (\xi - X_0)^2 + (\eta - Y_0)^2 = R^2 \end{bmatrix} \quad (25)$$

Figure 13:
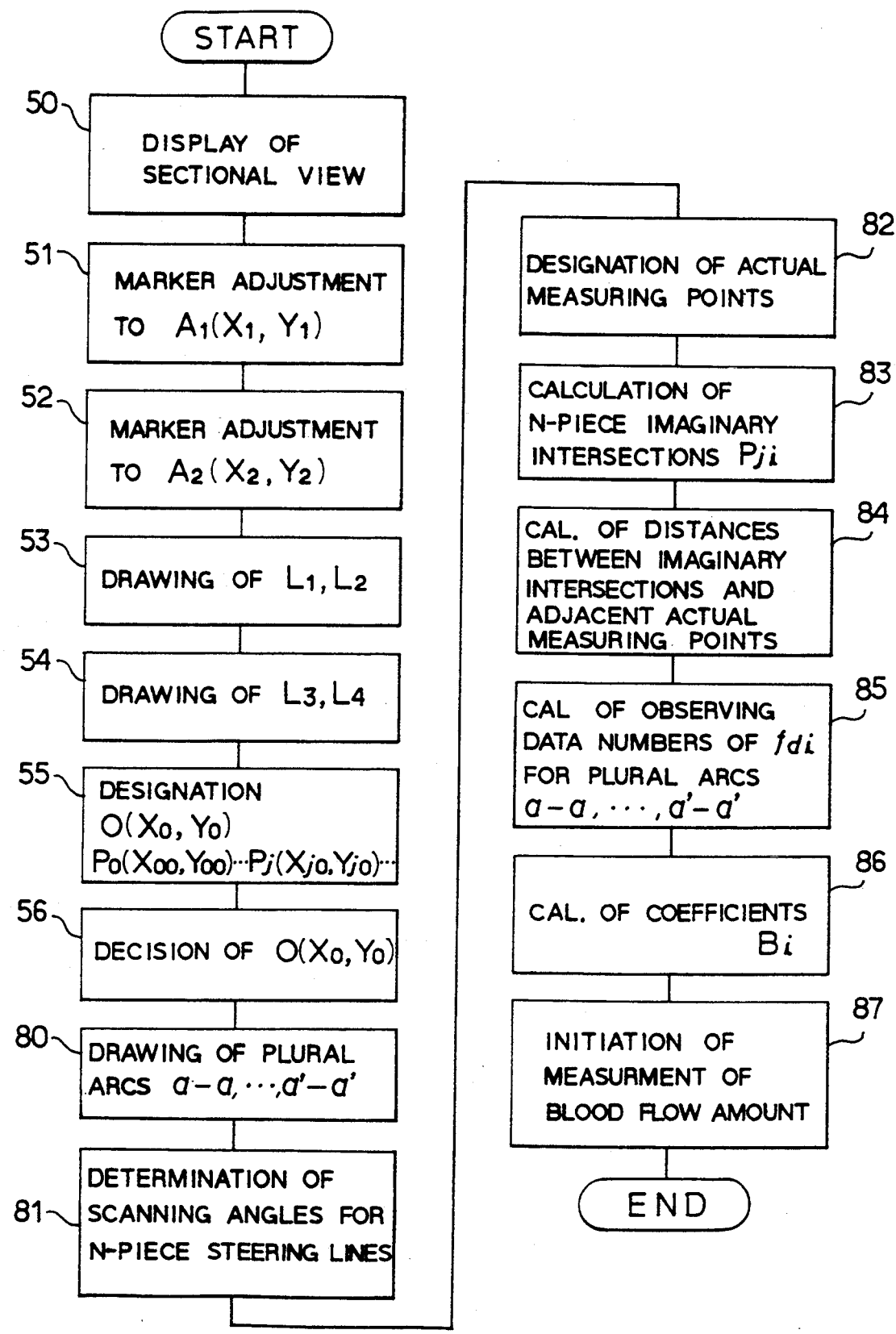
FIG. 13 is a flow chart carried out by a CPU of a third embodiment of the present invention.

In the present embodiment, the CPU 27 carries out a series of processes shown in FIG. 13. The processing of Steps 50 to 56 is the same as ones in FIG. 8 except that, at Step 55, a plurality of start points are drawn for plurality of arcs on the display 26.

After the crossed points O($X_0$, $Y_0$) of $L_3$ and $L_4$ being found at Step 56, Steps 80 to 87 are processed.

At Step 80, a plurality of arcs a—a, ..., a'—a' as parts of concentric circles are delineated. At Step 81, N-piece steering lines (N is two or more) is determined by a predetermined rule in wich they are arranged in a sector with an equal scanning angle and intersect the plurality of arcs a—a, ..., a'—a'. At Step 82, the intersections on the respective arcs a—a, ..., a'—a' are recognized as actual measuring points.

In contrast, at Step 83, imaginary intersections $P_{ji}$ of N-pieces are equally spaced on each arc and they are memorized. Then at Step 84, distances between each imaginary intersection $P_{ji}$ and its adjacent actual measuring points determined at Step 82 are calculated.

Figure 15:
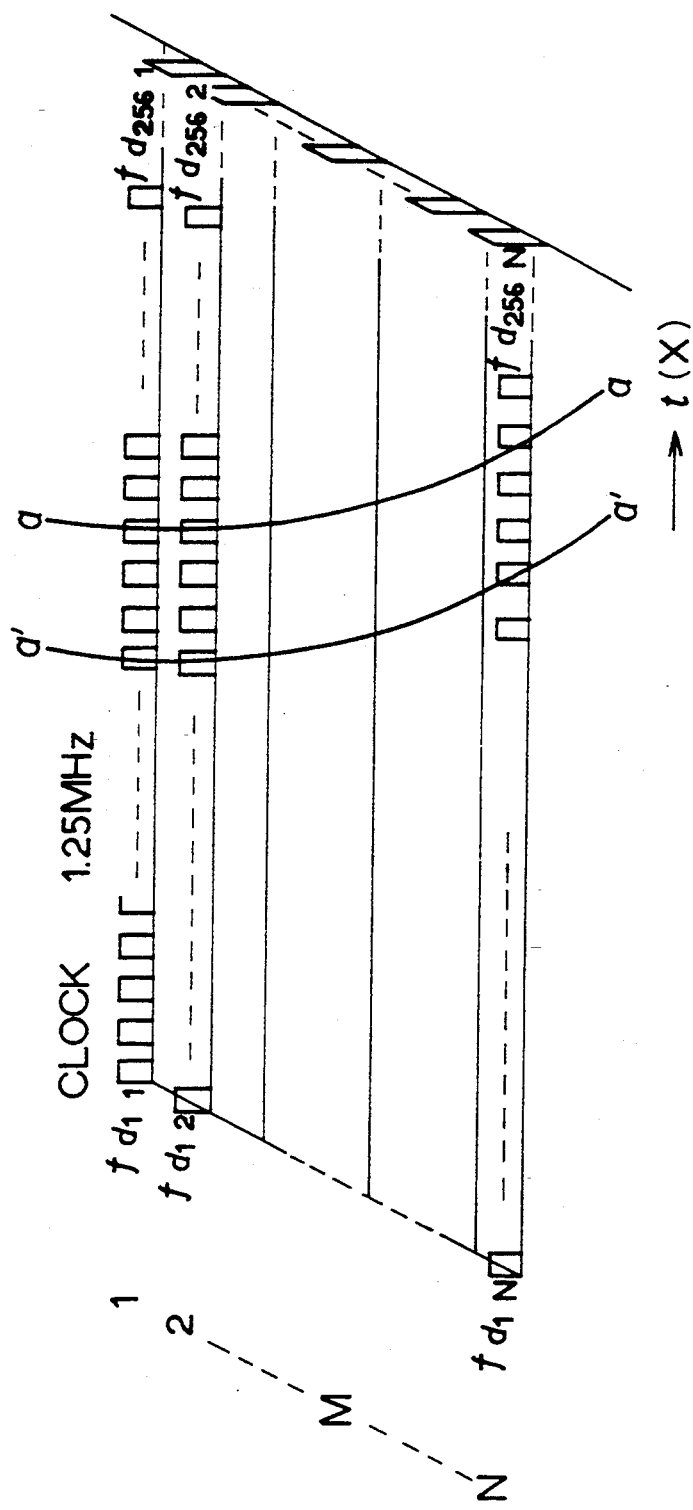
FIG. 15 is a time chart showing relation between drive pulses and plural arcs.

Then, at Step 85, it is calculated that the observing data numbers in compliance with the imaginary intersections $P_{ji}$ on the plural arcs a—a, ..., a'—a' are determined on an imaginary data map shown in FIG. 15, in the same manner as stated above. At Step 86, the coefficients $B_i$ for the imaginay intersections $P_{ji}$ are calculated for simplicity of calculation, also in the same manner already described.

Finally, at Step 87, the measurement is started by sending signals in regard to the imaginary measuring points $P_{ji}$ on each arc and the distances between the imaginary points and their adjacent actual measuring points, all of which are determined at Steps 82 to 84, in addition to the signals described before.

For the blood flow amount calculation section 24, as shown in FIG. 14, there provided further are a third memory 90, an weighted mean circuit 91 and an averaging circuit 92. The third memory 90 and the weighted mean circuit 91, which form an inferring section 93, are placed between the Doppler calculation section 23 and the multiplying circuit 33 of the calculation section 24. The averaging circuit 92 is connected to the output of the adding circuit 40.

The Doppler sift frequancy values $fd_i$ of the actual measuring points calculated by the Doppler calculation section 23 are sent to the third memory 90 to be stored frame by frame therein. The values thus stored are read out frame by frame and sent to the weighted mean circuit 91. The weighted mean circuit 91 receives signals of the imaginary points and distances determined at Steps 83 and 84 of FIG. 13. Hence, the weighted mean values for each of the imaginary measuring points $P_{ji}$ are calculated therein according to the equation (23).

The thus-calculated mean values are sent to the multiplying circuit 33, the second memory 34, and the adding circuit 40 in turn. Consequently, for each of the plurality of arcs a—a, ..., a'—a', the amount of blood flow is output to the averaging circuit 92. The amounts for all of the arcs a—a, ..., a'—a' are averaged by the averaging circuit 92, the averaged one being sent to the display 26, the chart recorder 25 and the cardiac output calculation section 70.

As a result, the amount of blood flow can also be obtained every certain period, that is, 25.6 msec in this case, and be displayed. In addition, since a plurality of arcs are employed, the precision in measurement is increased were remarkably than measurement utilizing a single arc.

In the present embodiment, as illustrated in FIG. 11, as many curved lines may be selected as possible (for example, up to 256) at each spacing of 0.6 mm in this case, and thus it is desirable that the amounts of blood flow, for example, on 8 curved lines (arcs) be calculated for increased precision through averaging.

The transmission and reception of the ultrasonic beams are repeated under the conditions where one steering line is formed of 8 rates at 5 kHz of the rate pulse frequency and where the number N of the steering lines is 16. From the output from the blood flow amount calculating section 24, one piece of data per 25.6 ms, that is, 39 pieces of data per second, can be obtained for one curved line a—a, and hence, for 4 curved lines a—a, ..., a'—a' an amount of data four times greater than that of one curved line for the same amount of required time can be obtained.

By the way, it is possible to directly calculate the foregoing equations (3), (4) and (6), or (16), (17) and (6) instead of adopting the coefficient $B_i$ in the calculation. In addition, it may be possible to omit the cardiac output calculation section 70 in FIG. 14, if necessary.

A sector electric scanning by ultrasonic beams has been described in the above embodiments, but the present invention is not limited to sector scanning as various kinds of scanning methods can be applied to the present invention. For example, an oblique scanning by using a linear array transducer, or the like, is suitable for measuring the amount of blood flow of a carotid and an artery vessel, or the amount of blood flow of a fetus.

Figure 16:
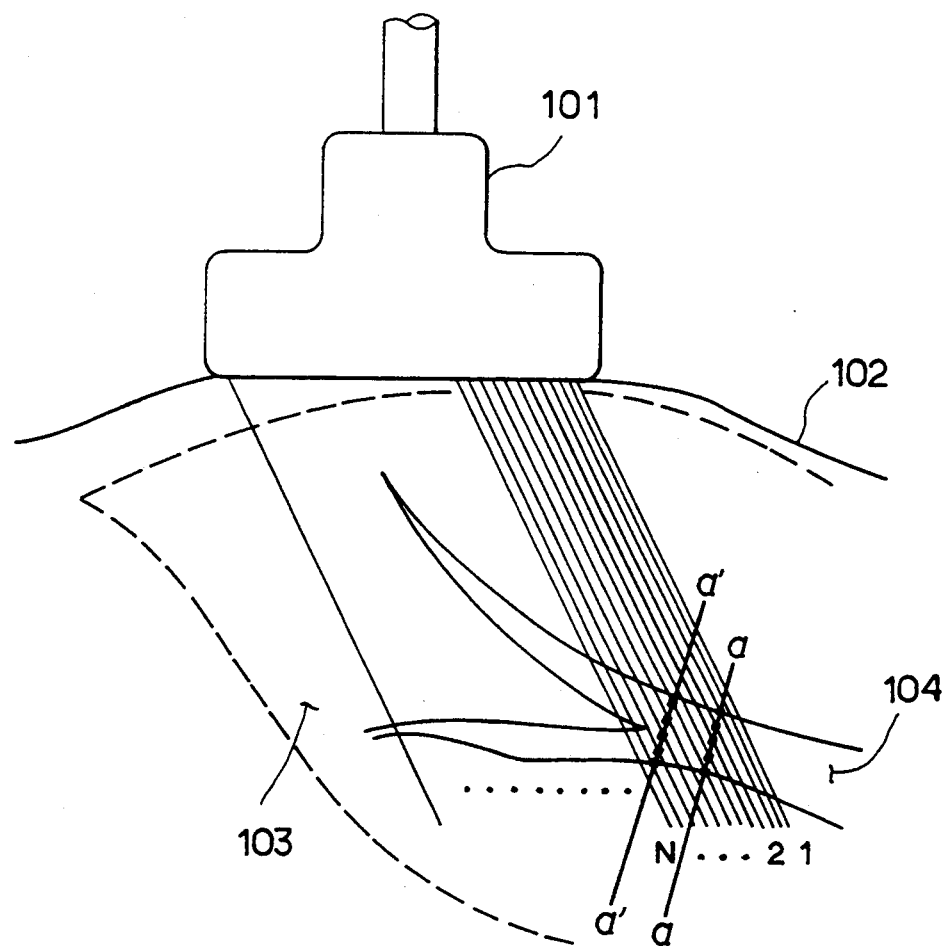
FIG. 16 is a schematic view showing an apparatus utilizing a linear steering.

FIG. 16 is a view explaining a case of measuring an amount of blood flow by performing the oblique scanning. Reference numeral 101 shows an ultrasonic probe including a linear array transducer; 102 represents a surface of a subject; 103 indicates a liver; and 104 shows a hepatic vein. Direct lines a—a, ..., a', ..., a' perpendicular to the directions of blood flows are determined while the real time B-mode image of the liver 103 is observed, thereby enabling the measurement of the blood flow of the hepatic vein 104 by the same principle as that of the embodiments as stated above.

Figure 17:
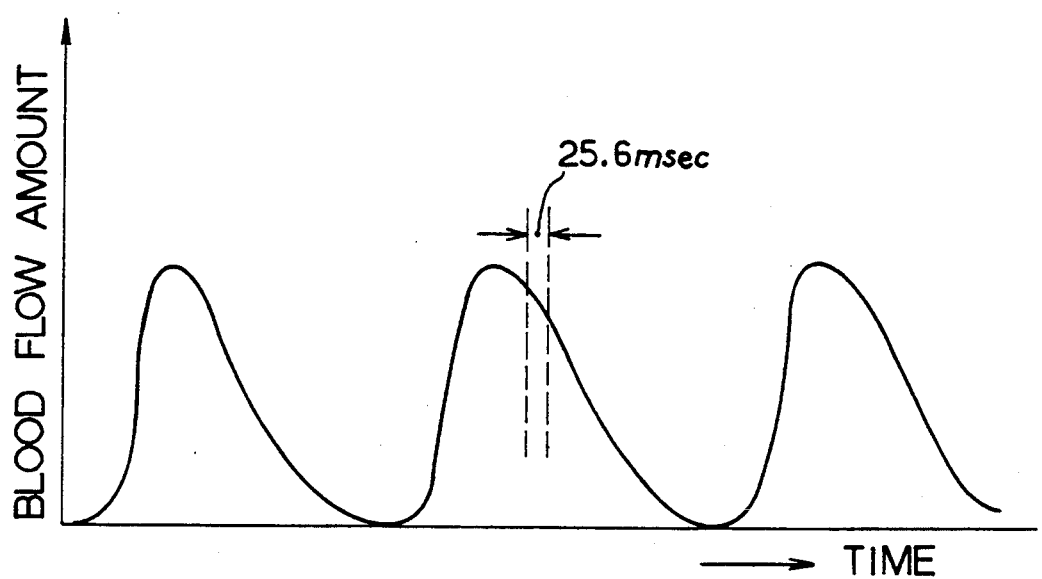
FIG. 17 is an example of display of the blood flow amount.

FIG. 17 shows an example of display of blood flow amount calculated in each of the above embodiments.

A fourth embodiment of the present invention will then be described with reference to FIG. 18.

Figure 18:
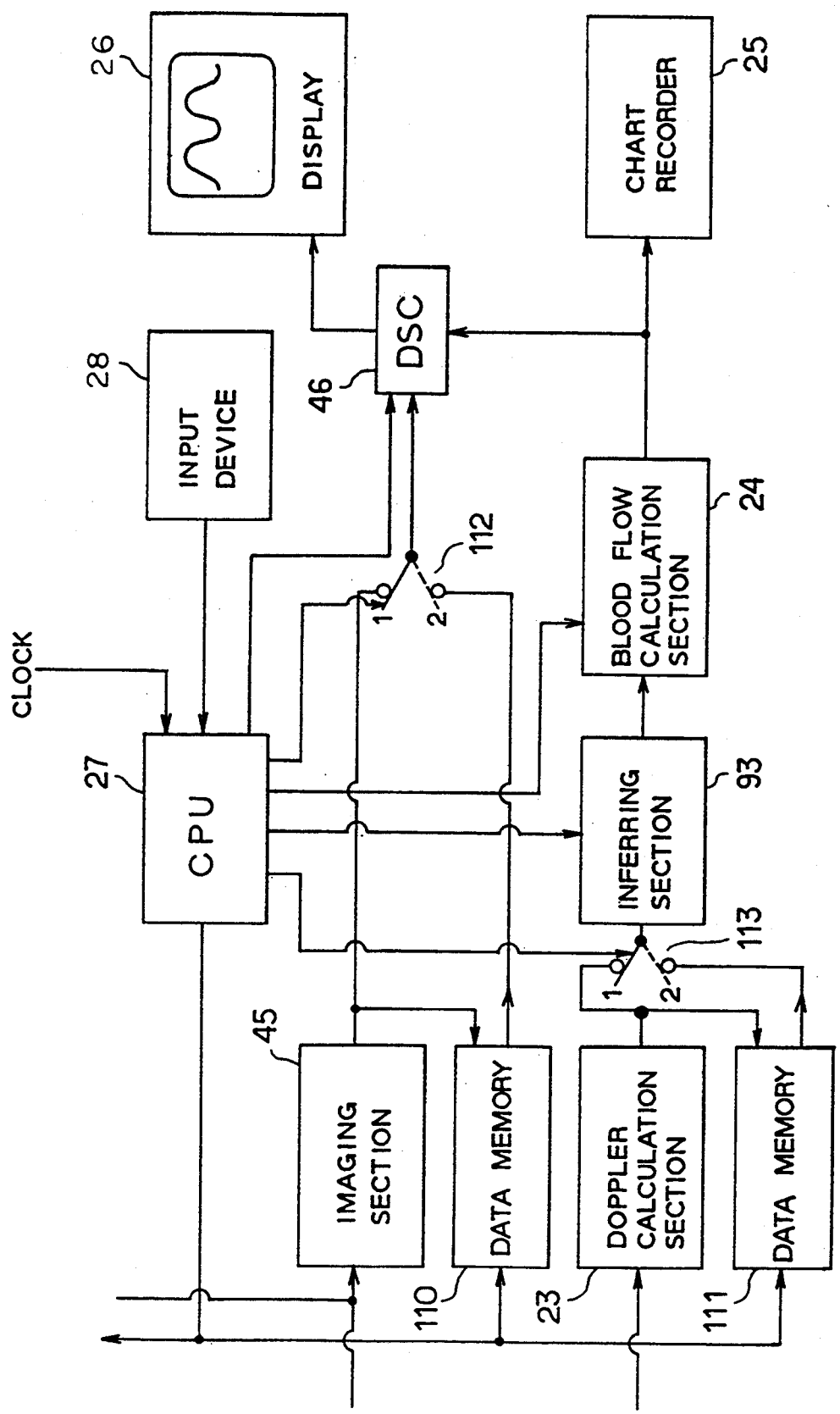
FIG. 18 is a view for showing a partial circuit diagram of an ultrasonic diagnosis apparatus according to a fourth embodiment of the present invention.

As shown in FIG. 18 in addition to the construction described in the third embodiment, there provided are two data memories 110 and 111, and two elctronic two-terminal switches 112 and 113, all of which are under control of the CPU 27.

In detail, the output of the imaging section 45 is connected to the input terminal of one data memory 110 and also to one switching terminal "1" of one switch 112. The output terminal of the data memory 110 is connected to the other switching terminal "2" of the switch 112, whose common terminal is conntected to the DSC 46. On one hand, the output of the Doppler calculation section 23 is connected to the input terminal of the other data memory 111 and to one switching terminal "1" of the other switch 113. The output terminal of the data memory 111 is connected to the other switching terminal "2" of the switch 113, whose common terminal is conntected to the blood flow amount calculation section 24 through the inferring section 93.

For measurement, both switches 112 and 113 are switched to their switching terminal "1" by the CPU 27. Then, an ultrasonic tomographic image and a marker of ultrasonic beams for Doppler detection are displayed on the display 26 to select an adequate direction of the marker. Thereby the ultrasonic beams are ready to be directed through a region of interest such as the aortic valve of a heart.

After this, ultrasonic beams are emitted and received through the probe 10 in response to control of the CPU 27. This permits the data of tomographic image to be stored into the data memory 110 and the data of Doppler signals to be stored into the data memory 111. This data store is carried out during a plurality of heartbeats (for instance, 10 beats).

Then, the switches 112 and 113 are switched back to their switching terminal "2" by the CPU 27, and the data stored in those data memories 110 and 111 are output repeatedly. The outputs from the data memory 110 are shown as tomographic images on the display 26, which are similar images as in real time measurement. Further, the outputs from the data memory 111 are supplied, as Doppler signals, to the inferring section 93. Therefore, the above processing results in that real time signals for the display 26 and inferring section 93 are replaced with repetition signals for plural heartbeats.

Then, one or more measuring lines are delineated on the display 26 by operator's choice and they are decided as observing data numbers on a data map shown in FIG. 15, for example. In the inferring section 93, making use of the data stored in the data memory 111, Doppler shift frequencies for imaginary measuring points equally spaced on the one or more measuring lines are inferred by means of the same manner(i.e., weighted mean calculation) explained before. Therefore, an amount of blood flow passing through a diagnostic region is obtained in the calculation section 24 according to the same principles previously mentioned.

As is apparent from the above, the operator can easily delineate one or more measuring lines on the display 26. The apparatus in the previously said embodiments requires the operator to use the both hands at the same time. Namely, the operator has to push the probe down to a patient body by the right hand (or left hand) and operate the input device for delineating the measuring lines by the left hand (or right hand), because tomographic images on the display should be observed in real time.

In this embodiment, however, it is not necessary to use the both hands at the same time, since tomographic image acquisition and measuring-line delineation are reasonably separated and can be done sequentially. As a result, the operation is simple, thus leading to more improved maneuverability and more accurate measuring-line delineation. Also, operation load is greatly reduced.

As stated above, embodiments of the present invention have been described, but it is understood that the present invention is not limited to the above embodiments and that the invention is suitably capable of other modified embodiments within the scope of the invention.

What we claim is:

1. An ultrasonic diagnosis apparatus comprising:
    means for generating a measuring line;
    means for forming an ultrasonic image of a diagnostic region of an object having flows of fluid therein;
    means for collecting information of velocity of the fluid at a plurality of measuring points on said measuring line provided on the ultrasonic image, said measuring line intersecting the flows of fluid at a substantially right angle to the direction of velocity of flow at each of said plurality of measuring points for which said velocity information is collected; and
    means for performing at least one of displaying and recording the information of velocity of the fluid in said direction of flow velocity perpendicular to said measuring line for said plurality of measuring points.

2. The ultrasonic diagnosis apparatus according to claim 1, wherein said forming means comprises:
    means for transmitting a plurality of ultrasonic beams for the diagnostic region and receiving echo signals of the plurality of ultrasonic beams, said plurality of ultrasonic beams containing at least a tomographic image signal and a Doppler shift signal;
    means for storing the echo signals containing the tomographic image signal and Doppler shift signal; and
    means for displaying a tomographic image as the ultrasonic image based on the tomographic image signal stored in the storing means,
    said collecting means comprising:
        means for designating the measuring line to intersect the flows of fluid at the substantially right angle on the tomographic image; and
        means for detecting the information of velocity of the fluid at the measuring points on the measuring line on the basis of the Doppler shift signal stored in the storing means.

3. The ultrasonic diagnosis apparatus according to claim 1, wherein said collecting means comprises:
    means for designating the measuring line to intersect the flows of fluid at the substantially right angle on the ultrasonic image;
    means for transmitting a plurality of ultrasonic beams for the measuring line and receiving echo signals of the plurality of ultrasonic beams; and
    means for detecting the information of velocity of the fluid at the plurality of measuring points on the measuring line, said plurality of ultrasonic beams passing through the measuring points.

4. The ultrasonic diagnosis apparatus according to claim 1, wherein said diagnostic region is a heart and said flows of fluid comprise flows of blood at the heart.

5. The ultrasonic diagnosis apparatus according to claim 1, wherein said performing means includes means for representing the velocity of the fluid with an elapsed time.

6. An ultrasonic diagnosis apparatus comprising:
    means for generating a measuring line;
    means for forming an ultrasonic image of a diagnostic region of an object having flows of fluid therein;
    means for collecting information of velocity of the fluid at a plurality of measuring points on said measuring line placed on the ultrasonic image, said measuring line intersecting the flows of fluid at a substantially right angle to the direction of velocity of flow at each of said plurality of measuring points for which said velocity information is collected; and
    means for calculating an amount of flows of the fluid on the basis of the information of velocity of the fluid in said direction of flow velocity perpendicular to said measuring line for said plurality of measuring points.

7. The ultrasonic diagnosis apparatus according to claim 6, wherein said forming means comprises:
    means for transmitting a plurality of ultrasonic beams for the diagnostic region and receiving echo signals of the plurality of ultrasonic beams, said plurality of ultrasonic beams containing at least a tomographic image signal and a Doppler shift signal;

means for storing the echo signals containing the tomographic image signal and Doppler shift signal; and means for displaying a tomographic image as the ultrasonic image based on the tomographic image signal stored in the storing means, said collecting means comprising:
   means for designating the measuring line to intersect the flows of fluid at the substantially right angle on the tomographic image; and
   means for detecting the information of velocity of the fluid at the measuring points on the measuring line on the basis of the Doppler shift signal stored in the storing means 8. The ultrasonic diagnosis apparatus according to claim 7, wherein said diagnostic region is a heart and said flows of fluid comprise flows of blood of the heart.

9. The ultrasonic diagnosis apparatus according to claim 7, wherein said detecting means includes means for post-calculating the information of velocity of the fluid at a plurality of imaginary measuring points as the plurality of measuring points on the measuring line by employing weighted mean calculation on the basis of the Doppler shift signal stored in the storing means.

10. The ultrasonic diagnosis apparatus according to claim 9, wherein said plurality of imaginary measuring points are equally spaced on the measuring line.

11. The ultrasonic diagnosis apparatus according to claim 10, wherein said measuring line is a single arc.

12. The ultrasonic diagnosis apparatus according to claim 6, wherein said collecting means comprises:
   means for designating the measuring line to intersect the flows of fluid at the substantially right angle on the ultrasonic image;
   means for transmitting a plurality of ultrasonic beams for the measuring line and receiving echo signals of the plurality of ultrasonic beams; and
   means for detecting the information of velocity of the fluid at the plurality of measuring points on the measuring line, said plurality of ultrasonic beams passing through the measuring points.

13. The ultrasonic diagnosis apparatus according to claim 12, wherein said diagnostic region is a liver.

14. The ultrasonic diagnosis apparatus according to claim 12, wherein said diagnostic region is a heart and said flows of fluid consist of flows of blood of the heart flowing from a left ventricle to an aorta through an aortic valve therein.

15. The ultrasonic diagnosis apparatus according to claim 12, further comprising means for performing at least either one of display and record of the amount of flows of the fluid.

16. The ultrasonic diagnosis apparatus according to claim 15, wherein said performing means includes means for representing the amount of flows of the fluid with an elapsed time.

17. The ultrasonic diagnosis apparatus according to claim 12, wherein said ultrasonic image is at least a B-mode tomographic image.

18. The ultrasonic diagnosis apparatus according to claim 12, wherein said ultrasonic image is a superimposed image of a B-mode tomographic image and a colour flow mapping of the fluid.

19. The ultrasonic diagnosis apparatus according to claim 12, wherein said measuring line consists of a plurality of measuring lines.

20. The ultrasonic diagnosis apparatus according to claim 19, wherein each of said plurality of measuring lines is an arc.

21. The ultrasonic diagnosis apparatus according to claim 20, wherein said collecting means further comprises means for post-calculating further information of velocity of the fluid at a plurality of imaginary measuring points on each of the measuring lines by employing weighted mean calculation on the basis of the information of velocity of the fluid detected by the detecting means and wherein said calculating means comprises means for calculating amounts of flows of the fluid corresponding to each of the arcs.

22. The ultrasonic diagnosis apparatus according to claim 21, wherein said imaginary measuring points are equally spaced on each of the plurality of arcs.

23. The ultrasonic diagnosis apparatus according to claim 22, wherein said calculating means includes means for averaging the amounts of flows of the fluid corresponding to the respective measuring lines.

24. An ultrasonic diagnosis apparatus comprising:
   means for generating a measuring line;
   means for forming an ultrasonic image of a diagnostic region of an object having flows of fluid therein;
   means for collecting information of velocity o the fluid at a plurality of measuring points on said measuring line placed on the ultrasonic image, said measuring line intersecting the flows of fluid at a substantially right angle to the direction of velocity of flow at each of said plurality of measuring points for which said velocity information is collected;
   first means for calculating a coefficient reflecting a geometric relation between the plurality of ultrasonic beams and the measuring line; and
   second means for calculating an amount of flows of the fluid by multiplying the information of velocity of the fluid in said direction of flow velocity perpendicular to said measuring line for said plurality of measuring points by the coefficient.

25. The ultrasonic diagnosis apparatus according to claim 24, wherein said forming means comprises:
   means for transmitting a plurality of ultrasonic beams for the diagnostic region and receiving echo signals of the plurality of ultrasonic beams, the beams containing at least a tomographic image signal and a Doppler shift signal;
   means for storing the echo signals containing the tomographic image signal and the Doppler shift signal; and
   means for displaying a tomographic image as the ultrasonic image based on the tomographic image signal stored in the storing means,
   said collecting means comprising
      means for designating the measuring line to intersect the flows of fluid at the substantially right angle on the tomographic image; and
      means for detecting the information of velocity of the fluid at the measuring points on the measuring line on the basis of the Doppler shift signal stored in the storing means.

26. The ultrasonic diagnosis apparatus according to claim 24, wherein said collecting means comprises
   means for designating the measuring line to intersect the flows of fluid at the substantially right angle on the ultrasonic image;

means for transmitting a plurality of ultrasonic beams for the plurality of measuring points on the measuring line and receiving echo signals of the plurality of ultrasonic beams; and means for detecting the information of velocity of flows of the fluid at the plurality of measuring points.

27. The ultrasonic diagnosis apparatus according to claim 26, wherein said detecting means includes means for calculating Doppler shift frequencies as the information of velocity of the fluid at the measuring points on the basis of the echo signals.

28. The ultrasonic diagnosis apparatus according to claim 27, wherein said diagnostic region comprises a heart having a left ventricle, an aortic valve, and an aorta, and wherein said flows of fluid comprise flows of blood flowing from the left ventricle to the aorta through the aortic valve.

29. The ultrasonic diagnosis apparatus according to claim 28, wherein said designating means includes means for providing three points on positions relating to the aortic valve on the ultrasonic image and for delineating an arc of a given radius as the measuring line based on the three points.

30. The ultrasonic diagnosis apparatus according to claim 29, wherein said arc comprises a single arc.

31. The ultrasonic diagnosis apparatus according to claim 30, wherein said collecting means further comprises means for providing equally-spaced points as the measuring points on the measuring line.

32. The ultrasonic diagnosis apparatus according to claim 31, wherein said transmitting/receiving means comprises means for scanning the plurality of ultrasonic beams in a form of an electrical sector through the measuring points.

33. The ultrasonic diagnosis apparatus according to claim 32, wherein said first calculating means comprises means for calculating the coefficient using intersection angles between the plurality of ultrasonic beams and the arc, the radius, a number of the equally-spaced measuring points, and coordinates of the three points.

34. The ultrasonic diagnosis apparatus according to claim 33, wherein said first calculating means includes a unit for calculating the scan angles using coordinates of the equally-spaced measuring points and a unit for calculating the intersection angles using the scan angles.

35. The ultrasonic diagnosis apparatus according to claim 28, further comprising means for calculating a cardiac output on the basis of the amount of flows of the blood.

36. The ultrasonic diagnosis apparatus according to claim 35, wherein said cardiac output calculating means comprises means for averaging the cardiac outputs at least two beats of the heart.

* * * * *

UNITED STATES PATENT AND TRADEMARK OFFICE
CERTIFICATE OF CORRECTION

PATENT NO. : 5,425,365
DATED : June 20, 1995
INVENTOR(S) : Kazuhiro IINUMA

It is certified that error appears in the above-indentified patent and that said Letters Patent is hereby corrected as shown below:

Claim 7, Column 19, Lines 2-3, there should be no line break between "beams" and "containing".

Claim 7, Column 19, Line 18, after "means" insert --.--.

Claim 24, Column 20, Line 28, change "o" to --of--.

Item [57]
Abstract, Line 5, change "trasnmitted" to --transmitted--.

Abstract, Line 11, change "frequancies" to --frequencies--.

Abstract, Line 14, change "obtaind" to --obtained--.

column 6, line 1, change "M" to --N--.

column 6, line 19, change "then" to --and--.

column 6, line 49, change "O($X_0, Y^0$)" to --O($X_0, Y_0$)--.

UNITED STATES PATENT AND TRADEMARK OFFICE
CERTIFICATE OF CORRECTION

PATENT NO. : 5,425,365
DATED : June 20, 1995
INVENTOR(S) : Kazuhiro IINUMA

It is certified that error appears in the above-indentified patent and that said Letters Patent is hereby corrected as shown below:

column 6, line 52, change "$P_0(X_{00}, Y^{00})$" to --$P_0(X_{00}, Y_{00})$--.

column 7, line 8, change "$1_{01}$" to --$\ell_{0i}$--.

column 7, line 31, change "$I_{01}$" to --$\ell_{0i}$--.

column 7, line 45, before.$fd_i$, change "m - 1 (M - 1)" to --M - 1 (M - $i$)--.

column 8, line 19, change "$\pi CW_0$" to --$\pi CW_0^2$--"

column 8, line 34, change "$i=1$" to --$i=M$--.

column 10, line 30, change ""$H.R_0/N$"" to --"$HxR_0/N$"--.

UNITED STATES PATENT AND TRADEMARK OFFICE
CERTIFICATE OF CORRECTION

PATENT NO. : 5,425,365
DATED : June 20, 1995
INVENTOR(S) : Kazuhiro IINUMA

It is certified that error appears in the above-indentified patent and that said Letters Patent is hereby corrected as shown below:

column 10, line 34, change ""$H.R_0/2N$"" to --"$HxR_0/2N$"--.

column 10, line 36, change ""$H.R_0/2N$"" to --"$HxR_0/2N$"--.

column 10, line 54, change "$fd_{11}, fd_{21},$" to --$fd_{1\ 1}, fd_{2\ 1},$--.

column 10, line 56, change "$fd_{12}, fd_{22},$" to --$fd_{1\ 2}, fd_{2\ 2},$--.

column 12, line 19, change "$fd_{11}, fd_{21}, ..., fd_{256\ 1}, fd_{12},$" to --$fd_{1\ 1}, fd_{2\ 1}, ..., fd_{256\ 1}, fd_{1\ 2},$--

UNITED STATES PATENT AND TRADEMARK OFFICE
CERTIFICATE OF CORRECTION

PATENT NO. : 5,425,365
DATED : June 20, 1995
INVENTOR(S) : Kazuhiro IINUMA

It is certified that error appears in the above-indentified patent and that said Letters Patent is hereby corrected as shown below:

column 12, line 20, change "$fd_{22},$" to --$fd_{2\ 2},$--.

column 14, line 57, change "$\varepsilon^+, \theta^+$" --$\xi^+, \eta^+$--.

Signed and Sealed this

Eighteenth Day of June, 1996

BRUCE LEHMAN

*Attest:*

*Attesting Officer*    *Commissioner of Patents and Trademarks*